United States Patent
Yang et al.

(10) Patent No.: US 12,359,169 B2
(45) Date of Patent: Jul. 15, 2025

(54) UNIVERSAL CAR-T CELL AND PREPARATION METHOD AND USE THEREOF

(71) Applicant: SHANGHAI LONGYAO BIOTECHNOLOGY INC., LTD., Shanghai (CN)

(72) Inventors: Xuanming Yang, Shanghai (CN); Yangxin Fu, Shanghai (CN); Xin Wang, Shanghai (CN); Shengqin Ye, Shanghai (CN); Xiaoqing Zhang, Shanghai (CN)

(73) Assignee: SHANGHAI LONGYAO BIOTECHNOLOGY INC., LTD., Shanghai (CN)

( * ) Notice: Subject to any disclaimer, the term of this patent is extended or adjusted under 35 U.S.C. 154(b) by 609 days.

(21) Appl. No.: 17/681,167

(22) Filed: Feb. 25, 2022

(65) Prior Publication Data
US 2022/0175840 A1    Jun. 9, 2022

Related U.S. Application Data

(63) Continuation-in-part of application No. 17/126,840, filed on Dec. 18, 2020, now abandoned, which is a continuation of application No. PCT/CN2019/077921, filed on Mar. 13, 2019.

(30) Foreign Application Priority Data

Jun. 20, 2018   (CN) .......................... 201810636386.3

(51) Int. Cl.
| | |
|---|---|
| C12N 5/00 | (2006.01) |
| A61K 40/11 | (2025.01) |
| A61K 40/22 | (2025.01) |
| A61K 40/31 | (2025.01) |
| A61K 40/41 | (2025.01) |
| A61K 40/42 | (2025.01) |
| A61P 35/00 | (2006.01) |
| C07K 14/725 | (2006.01) |
| C12N 5/0783 | (2010.01) |
| C12N 15/86 | (2006.01) |

(52) U.S. Cl.
CPC ............ *C12N 5/0636* (2013.01); *A61K 40/11* (2025.01); *A61K 40/22* (2025.01); *A61K 40/31* (2025.01); *A61K 40/418* (2025.01); *A61K 40/421* (2025.01); *A61K 40/4221* (2025.01); *A61P 35/00* (2018.01); *C07K 14/7051* (2013.01); *C12N 15/86* (2013.01); *A61K 2239/38* (2023.05); *A61K 2239/48* (2023.05)

(58) Field of Classification Search
CPC .............................. C12N 5/0636; A61K 40/42
See application file for complete search history.

(56) References Cited

U.S. PATENT DOCUMENTS

| | | | |
|---|---|---|---|
| 9,273,283 | B2 | 3/2016 | Sentman |
| 9,663,763 | B2 | 5/2017 | Sentman |
| 2012/0302466 | A1 | 11/2012 | Sentman |
| 2016/0312182 | A1 | 10/2016 | Sentman |
| 2017/0253857 | A1 | 9/2017 | Sentman |

FOREIGN PATENT DOCUMENTS

| | | | | |
|---|---|---|---|---|
| CN | 104395463 A | 3/2015 | | |
| CN | 106544321 A | 3/2017 | | |
| WO | 2017180989 A2 | 10/2017 | | |
| WO | WO2018132479 A1 * | 7/2018 | ........... | C12N 5/0783 |
| WO | 2019232444 A1 | 12/2019 | | |
| WO | WO2020156335 A1 * | 8/2020 | ............ | C07K 16/28 |

OTHER PUBLICATIONS

Liu et al. (2017) "CRISPR-Cas9-mediated multiplex gene editing in CAR-T cells" Cell research, 27(1), 154-157. (Year: 2017).*
Bonini et al. (1997) "HSV-TK gene transfer into donor lymphocytes for control of allogeneic graft-versus-leukemia" Science, 276(5319), 1719-1724. (Year: 1997).*
PCT/CN2019/077921 International Search Report dated Jun. 18, 2019.
Beckman Coulter, "SW28 and SW28.1 Rotors," Used in Beckman Coulter Class H, R, and S Preparative Ultracentrifuges, Jan. 2006, 28 pages; 2006.
Bonini, Chiara, et al., "HSV-TK Gene Transfer Into Donor Lynphocytes for Control of Allogeneic Graft-Versus-Leukemia," Science 276 (5319), 1719-1724, published Jun. 13, 1997.
Fellmann, Christof, et al., "Cornerstones of CRISPR-Cas in drug discovery and therapy," Nature Reviews Drug Discovery, vol. 16, pp. 89-100, Feb. 2017; published online Dec. 2016.
Fuss, Ivan J., et al., "Isolation of Whole Mononuclear Cells from Peripheral Blood and Cord Blood," Curr. Protoc. Innunol., 2009, 85:7.1.1-7.1.8; Supplement 85, Apr. 2009; John Wiley & Sons, Inc.
Humbert, Olivier, et al., "Development of Third-generation Cocal Envelope Producer Cell Lines for Robust Lentiviral Gene Transfer into Hematopoietic Stem Cells and T-Cells," Molecular Therapy, vol. 24, No. 7, pp. 1237-1246; Jul. 2016, Am. Society of Gene & Cell Therapy.
Legut, Mateusz, et al., "CRISPR-mediated TCR replacement generates superior anticancer transgenic T cells," Blood 2018, 131(3):311-322; Jan. 18, 2018; published online Nov. 2017; Am. Society of Hematology.

(Continued)

*Primary Examiner* — Laura Schuberg
*Assistant Examiner* — James Joseph Graber
(74) *Attorney, Agent, or Firm* — Sughrue Mion, PLLC

(57) ABSTRACT

Disclosed are a universal CAR-T cell knocking out one or more of CD3 delta, CD3 gamma, CD3 epsilon and CD3 zeta, and simultaneously introducing the HSV-TK gene. Also disclosed are a method for preparing the above-mentioned CAR-T cell, a preparation comprising the CAR-T cell, and the use of the CAR-T cell.

5 Claims, 9 Drawing Sheets

Specification includes a Sequence Listing.

(56) References Cited

OTHER PUBLICATIONS

Liu, Xiaojuan, et al., "CRISPR-Cas9-mediated multiplex gene editing in CAR-T cells," Cell Research, Letter to the Editor, 2017, 27:154-157; published online Dec. 6, 2016.
Ren, Jiangtao, et al., Multiplex Genome Editing to Generate Universal CAR T Cells Resistant to PD1 Inhibition, Clin. Cancer Res., Nov. 4, 2016.
Tiscornia, Gustavo, et al., "Production and purification of lentiviral vectors," Nature Protocols, vol. 1, No. 1, pp. 241-245, published online Jun. 27, 2006.
Torikai, Hiroki, et al., "A foundation for universal T-cell based immunotherapy: t cells engineered to express a CD19-specific chimeric-antigen-receptor and elimate expression of endogenous TCR," Blood, vol. 119, No. 24, pp. 5697-5705, Jun. 14, 2012.

* cited by examiner

UNIVERSAL CAR-T CELL AND PREPARATION METHOD AND USE THEREOF

The present application is a continuation-in-part of U.S. patent application Ser. No. 17/126,840, filed Dec. 18, 2020, a continuation of PCT/CN2019/077921, filed Mar. 13, 2019, which claims the benefit of CN application 201810636386.3 (CN), filed Jun. 20, 2018, all of which are hereby incorporated by reference in their entireties herein.

TECHNICAL FIELD

The present invention relates to the technical field of cell immunotherapy, especially relates to a universal CAR-T cell and a preparation method thereof and use thereof.

BACKGROUND OF THE INVENTION

The use of immunological therapy for overcoming tumors has always been an important direction in the application of immunology in translational medicine. With the development of various omics (genomics, proteomics, etc.), tumor cells have been widely recognized due to their immunogenicity caused by mutations, which lays a theoretical foundation for tumor immunotherapy. At the same time, with the accumulation of tumor immunology research itself, tumor immunotherapy has recently made a great progress, and a series of new immunotherapy methods have gradually entered into the clinic. The current tumor immunology research has established the central position of T cell killing in tumor immunotherapy, and the chimeric antigen receptor T cell (CAR-T cell) is a tumor-killing cell which has combined the targeted recognition of antibody and the tumor-killing function of T cell, and been generated by artificial modification.

The concept of chimeric antigen receptor T cell was first proposed by Gross, Waks and Eshhar in 1989. They expressed TNP-recognizing antibodies on T cells, achieving antigen-specific, non-MHC-restricted T cell activation and enhanced effect, and proposed the concept of the application of CAR-T technology in tumor treatment. According to this principle, tumor-specific antibodies are embedded into T cells, which will give T cells new tumor-killing capabilities. After that, CAR-T technology was introduced into anti-tumor clinical trials, but the final clinical results of early CAR-T cells are not ideal since their intracellular signal transmission domain contains only the first signal, and the selected tumor type is a solid tumor. In 2008, the Fred Hutchison Cancer Institute and other institutions used CAR-T to treat B cell lymphoma, although the treatment results are not ideal, the key to this clinical trial is to demonstrate that CAR-T treatment with CD20-expressing B cells as the target is relatively safe. Subsequently, in 2010, NCI reported a case of successful treatment of B-cell lymphoma, using CAR-T targeting CD19, the patient's lymphoma was controlled, normal B cells were also eliminated, and serum Ig was significantly reduced, providing a theoretical and practical support for the effectiveness of CAR-T in the treatment of B cell-derived lymphomas. In 2011, a team led by Dr. Carl June of the University of Pennsylvania in the United States used CAR-T that specifically recognizes CD19 for the treatment of chronic lymphocytic leukemia derived from B cells, showing a "cure" effect. After that, clinical trials have been launched in relapsed and refractory acute lymphoblastic cell leukemia, and good results have also been achieved. Due to this breakthrough progress and the development of other immune regulation methods, Science magazine ranked tumor immunotherapy as the number one scientific and technological breakthrough in 2013. This success has caused widespread influence in countries around the world, and countries have begun to carry out a large number of CAR-T-based scientific research and clinical trials of tumor treatment.

The structure of CAR consists of an extracellular antigen recognition domain, an extracellular hinge region, a transmembrane domain, and an intracellular signal transduction domain. The extracellular antigen recognition domain generally consists of a single-chain antibody, which specifically recognizes membrane surface molecules of the tumor cell, or can be a ligand or a receptor of some tumor-specific antigens, etc. The extracellular hinge region is a spatial structure that separates the antigen binding domain from the transmembrane domain, and its purpose is to provide a suitable spatial position, so that the extracellular antigen recognition domain can maintain the correct structure and transmit the intracellular signals before and after recognizing the antigen. The transmembrane domain is a domain for ensuring the positioning of the CAR molecule on the membrane surface. The intracellular signal transduction domain is a key part of mediating the CAR signal transduction, and is usually a combination of one or several first signals (for the recognition of TCR and MHC-I-peptide complex) and second signals (for the recognition of costimulatory receptor and costimulatory ligand). The first-generation CAR contains only the first signal, the second-generation CAR has one first signal and one second signal, and the third-generation CAR has one first signal and two second signal domains. Although CAR-T has achieved a great success in the treatment of leukemia derived from B cell, its relatively high recurrence rate and low effectiveness for solid tumors are important challenges currently. Therefore, there is currently an urgent clinic need of developing a new generation of high-efficiency CAR-T. In addition to the third-generation CAR-T, there are currently other new CAR-T design strategies, that is, introducing new regulatory molecules independent of CAR on the basis of the second-generation CAR-T to further enhance the function of CAR-T.

The application of CAR-T targeting the B cell surface-targeting molecules CD19 and CD20 prepared from the patient's own blood cells in the treatment of B cell leukemia has been relatively mature, but the entire process is complicated and time-consuming, while the autoimmune cells are not convenient to use as a source of T-cells for CAR-T for some special patients, such as those with serious conditions, poor quality of cells, or AIDS associated lymphoma. Although CAR-T has achieved a great success in the treatment of leukemia derived from B cells, the entire CAR-T treatment is time-consuming and has patient heterogeneity. Some patients cannot effectively produce CAR-T cells due to their own cell defects. These limit the application range of CAR-T. The development of universal CAR-T will largely solve these challenges.

Currently, all the clinic universal CAR-T protocols use CRISPR/Cas9 or TALEN gene editing means to knock out TCR so as to avoid the GVHD effect. Any other preparation method of universal CAR-T that can effectively avoid the GVHD effect and the combination with a CAR-T close switch have yet not been reported.

SUMMARY OF THE INVENTION

The present invention aims to address the defects in the prior art, provides an universal CAR-T cell, which achieves an effect of avoiding GVHD effect by knocking out CD3Delta, CD3Gamma, CD3 Epsilon and CD3 zeta, and introduces the HSV-TK gene. When a side effect occurs, it can be treated by the clinically existing ganciclovir to remove the CAR-T cells.

To achieve the aforesaid object, the present disclosure provides a universal CAR-T cell in which one or more of CD3Delta, CD3Gamma, CD3 Epsilon and CD3 zeta is knocked out.

In some embodiments, said CD3Delta, CD3Gamma, CD3 Epsilon or CD3 zeta is knocked out by administering the CRISPER/cas9 system to CAR-T cell.

In some embodiments, said CD3Delta, CD3Gamma, CD3 Epsilon or CD3 zeta is knocked out by administering the KO CD3Delta sgRNA, KO CD3Gamma sgRNA, KO CD3 Epsilon sgRNA or KO CD3 zeta sgRNA to CAR-T cell.

In some embodiments, said KO CD3Delta sgRNA comprises the nucleotide sequence set forth in any one of SEQ ID NO:1-2.

In some embodiments, said KO CD3Gamma sgRNA comprises the nucleotide sequence set forth in any one of SEQ ID NO:3-5.

In some embodiments, said KO CD3 Epsilon sgRNA comprises the nucleotide sequence set forth in any one of SEQ ID NO: 6-7.

In some embodiments, said KO CD3 zeta sgRNA comprises the nucleotide sequence set forth in any one of SEQ ID NO: 8-10.

In some embodiments, the knockout further includes administering Cas9 protein to the CAR-T cell.

In some embodiments, the CAR-T cell comprises a nucleic acid encoding a chimeric antigen receptor (CAR), and the CAR includes an extracellular antigen recognition domain, a hinge region, a transmembrane domain, an intracellular signal transduction domain.

In some embodiments, the extracellular antigen recognition domain comprises a single chain antibody or a ligand or receptor of a tumor-specific antigen.

In some embodiments, wherein the single chain antibody comprises an anti-CD19 antibody, an anti-CD20 antibody, an anti-EGFR antibody, an anti-HER2 antibody or an anti-EGFRVIII antibody.

In some embodiments, the anti-CD20 antibody comprises the amino acid sequence set forth in any one of SEQ ID NO: 11.

In some embodiments, the anti-CD19 antibody comprises the amino acid sequence set forth in any one of SEQ ID NO: 24.

In some embodiments, wherein the ligand or receptor of tumor-specific antigen comprises NKG2D.

In some embodiments, the transmembrane domain includes one protein derived from a protein selected from the group consisting of CD8a, CD28, CD137 and/or CD3.

In some embodiments, the hinge region connects the extracellular antigen recognition domain with the transmembrane domain, and includes a hinge region of protein selected from the group consisting of IgG hinge region and CD8a hinge region.

In some embodiments, the intracellular signal transduction domain further includes at least one of CD3Delta, CD3Gamma, CD3 Epsilon, CD3 zeta, CD28, CD137, 4-1BB, ICOS, OX40, IL-12, TL7R and TL2R.

Further, the intracellular signal transduction domain comprises a costimulatory domain, and a primary signal transduction domain.

In some embodiments, the costimulatory domain comprises a costimulatory domain of protein selected from the group consisting of CD137, CD28, 4-1BB, OX40 and ICOS.

In some embodiments, the primary signal transduction domain comprises a functional signal transduction domain of protein selected from the group consisting of CD3Delta, CD3Gamma, CD3 Epsilon and CD3 zeta.

In some embodiments, the CAR includes an extracellular antigen recognition domain, a CD8a hinge region, a CD8a transmembrane domain, a 4-1BB costimulatory domain and a CD3 zeta signal transduction domain.

In some embodiments, the CAR further includes a kappa leader sequence or a CD8 signal peptide.

In some embodiments, the CAR includes a kappa leader sequence, an extracellular antigen recognition domain, a CD8a hinge region, a CD8a transmembrane domain, a 4-1BB costimulatory domain and a CD3 zeta signal transduction domain.

In some embodiments, the kappa leader sequence comprises the amino acid sequence set forth in SEQ ID NO: 16.

In some embodiments, the CD8 signal peptide comprises the amino acid sequence set forth in SEQ ID NO: 17.

In some embodiments, the CD8a hinge region comprises the amino acid sequence set forth in SEQ ID NO: 12.

In some embodiments, the CD8a transmembrane domain comprises the amino acid sequence set forth in SEQ ID NO:13.

In some embodiments, the 4-1BB costimulatory domain comprises the amino acid sequence set forth in SEQ ID NO: 14.

In some embodiments, the CD3 zeta signal transduction domain comprises the amino acid sequence set forth in SEQ ID NO: 15.

In some embodiments, the CAR includes an anti-CD19 CAR, an anti-CD20 CAR, an anti-EGFR CAR, an anti-HER2 CAR or an anti-EGFRVIII CAR.

In some embodiments, the anti-CD20 CAR comprises the amino acid sequence set forth in SEQ ID NO: 18.

In some embodiments, the anti-CD19 CAR comprises the amino acid sequence set forth in SEQ ID NO: 25.

In some embodiments, the nucleic acid encoding the anti-CD20 CAR comprises the nucleotide sequence set forth in any one of SEQ ID NO. 22.

In some embodiments, the nucleic acid encoding the anti-CD19 CAR comprises the nucleotide sequence set forth in any one of SEQ ID NO. 28.

In some embodiments, the CAR-T cell comprises a nucleic acid encoding HSV-TK gene.

In some embodiments, the HSV-TK gene comprises the nucleotide sequence set forth in SEQ ID NO: 30.

In some embodiments, the nucleic acid encoding a CAR is located in the same vector as the nucleic acid encoding HSV-TK gene.

In some embodiments, the nucleic acid encoding CAR is linked to the nucleic acid encoding HSV-TK gene by a nucleic acid encoding a 2A peptide.

In some embodiments, the 2A peptide comprises the amino acid sequence set forth in SEQ ID NO: 19.

In some embodiments, the vector comprises the nucleotide sequence set forth in SEQ ID NO: 23 or SEQ ID NO: 29.

In some embodiments, the CAR-T cell comprises a nucleic acid comprising the nucleotide sequence set forth in SEQ ID NO: 23 or SEQ ID NO: 29.

In some embodiments, the CAR-T cell is allogeneic CAR-T cells

In some embodiments, the CAR-T cell is derived from cord blood or peripheral blood.

The present disclosure further provides a method of preparing a universal CAR-T cell, including the following steps: one or more of CD3Delta, CD3Gamma, CD3 Epsilon and CD3 zeta is knocked out in the CAR-T cell by a suitable gene knockout method.

In some embodiments, the method the following steps: one or more of CD3Delta, CD3Gamma, CD3 Epsilon and CD3 zeta is knocked out in the CAR-T cell by CRISPER/cas9 system.

In some embodiments, the method the following steps: one or more of CD3Delta, CD3Gamma, CD3 Epsilon and CD3 zeta is knocked out in the CAR-T cell by administering the KO CD3Delta sgRNA, KO CD3Gamma sgRNA, KO CD3 Epsilon sgRNA or KO CD3 zeta sgRNA to CAR-T cell, Wherein said KO CD3Delta sgRNA comprises the nucleotide sequence set forth in any one of SEQ ID NO:1-2, said KO CD3Gamma sgRNA comprises the nucleotide sequence set forth in any one of SEQ ID NO: 3-5, said KO CD3 Epsilon sgRNA comprises the nucleotide sequence set forth in any one of SEQ ID NO: 6-7, said KO CD3 zeta sgRNA comprises the nucleotide sequence set forth in any one of SEQ ID NO: 8-10.

In some embodiments, the method further comprises administering Cas9 protein to the CAR-T cell.

In some embodiments, the method comprises transducing a CAR to the CAR-T cell.

In some embodiments, the CAR includes an extracellular antigen recognition domain, a hinge region, a transmembrane domain, an intracellular signal transduction domain.

In some embodiments, the extracellular antigen recognition domain comprises a single chain antibody or a ligand or receptor of a tumor-specific antigen.

In some embodiments, wherein the single chain antibody comprises an anti-CD19 antibody, an anti-CD20 antibody, an anti-EGFR antibody, an anti-HER2 antibody or an anti-EGFRVIII antibody.

In some embodiments, the anti-CD20 antibody comprises the amino acid sequence set forth in any one of SEQ ID NO: 11.

In some embodiments, the anti-CD19 antibody comprises the amino acid sequence set forth in any one of SEQ ID NO: 24.

In some embodiments, wherein the ligand or receptor of tumor-specific antigen comprises NKG2D.

In some embodiments, the transmembrane domain includes one protein derived from a protein selected from the group consisting of CD8a, CD28, CD137 and/or CD3.

In some embodiments, the hinge region connects the extracellular antigen recognition domain with the transmembrane domain, and includes a hinge region of protein selected from the group consisting of IgG hinge region and CD8a hinge region.

In some embodiments, the intracellular signal transduction domain further includes at least one of CD3Delta, CD3Gamma, CD3 Epsilon, CD3 zeta, CD28, CD137, 4-1BB, ICOS, OX40, IL-12, TL7R and TL2R.

Further, the intracellular signal transduction domain comprises a costimulatory domain, and a primary signal transduction domain.

In some embodiments, the costimulatory domain comprises a costimulatory domain of protein selected from the group consisting of CD137, CD28, 4-1BB, OX40 and ICOS.

In some embodiments, the primary signal transduction domain comprises a functional signal transduction domain of protein selected from the group consisting of CD3Delta, CD3Gamma, CD3 Epsilon and CD3 zeta.

In some embodiments, the CAR includes an extracellular antigen recognition domain, a CD8a hinge region, a CD8a transmembrane domain, a 4-1BB costimulatory domain and a CD3 zeta signal transduction domain.

In some embodiments, the CAR further includes a kappa leader sequence or a CD8 signal peptide.

In some embodiments, the CAR includes a kappa leader sequence, an e extracellular antigen recognition domain, a CD8a hinge region, a CD8a transmembrane domain, a 4-1BB costimulatory domain and a CD3 zeta signal transduction domain.

In some embodiments, the kappa leader sequence comprises the amino acid sequence set forth in SEQ ID NO: 16.

In some embodiments, the CD8 signal peptide comprises the amino acid sequence set forth in SEQ ID NO: 17.

In some embodiments, the CD8a hinge region comprises the amino acid sequence set forth in SEQ ID NO: 12.

In some embodiments, the CD8a transmembrane domain comprises the amino acid sequence set forth in SEQ ID NO:13.

In some embodiments, the 4-1BB costimulatory domain comprises the amino acid sequence set forth in SEQ ID NO: 14.

In some embodiments, the CD3 zeta signal transduction domain comprises the amino acid sequence set forth in SEQ ID NO: 15.

In some embodiments, the CAR includes an anti-CD19 CAR, an anti-CD20 CAR, an anti-EGFR CAR, an anti-HER2 CAR or an anti-EGFRVIII CAR.

In some embodiments, the anti-CD20 CAR comprises the amino acid sequence set forth in SEQ ID NO: 18.

In some embodiments, the anti-CD19 CAR comprises the amino acid sequence set forth in SEQ ID NO: 25.

In some embodiments, the nucleic acid encoding the anti-CD20 CAR comprises the nucleotide sequence set forth in any one of SEQ ID NO. 22.

In some embodiments, the nucleic acid encoding the anti-CD19 CAR comprises the nucleotide sequence set forth in any one of SEQ ID NO. 28.

In some embodiments, the method comprises introducing an HSV-TK gene into the CAR-T cell.

In some embodiments, the HSV-TK gene comprises the nucleotide sequence set forth in SEQ ID NO: 30.

In some embodiments, the method comprises introducing a vector into the CAR-T cell, wherein the vector comprises the nucleic acid encoding a CAR and the nucleic acid encoding HSV-TK gene.

In some embodiments, the nucleic acid encoding CAR is linked to the nucleic acid encoding HSV-TK gene by a nucleic acid encoding a 2A peptide.

In some embodiments, the 2A peptide comprises the amino acid sequence set forth in SEQ ID NO: 19.

In some embodiments, the vector comprises the nucleotide sequence set forth in SEQ ID NO: 23 or SEQ ID NO: 29.

In some embodiments, the CAR-T cell is allogeneic CAR-T cells

In some embodiments, the CAR-T cell is derived from cord blood or peripheral blood.

Further, the universal CAR-T cell is prepared by a gene knockout method comprising the following steps:
  step 1: construction of lentiviral vector and production of virus:
    designing an sgRNA for one or more of CD3Delta, CD3Gamma, CD3 Epsilon and CD3 zeta, cloning the sgRNA into pLenti-CrisprV2;
    co-transfecting the pLenti-CrisprV2 with lentiviral packaging plasmid;
    collecting a supernatant after a predetermined period of time;
    filtering the supernatant and
    centrifugating and concentrating the virus, to obtain a pLenti-CRISPRV2-sgRNA virus;
  step 2: preparation of CD3-negative CAR-T cell:
    isolating and purifying mononuclear cell,
    inoculating the isolated and purified mononuclear cell into a culture plate comprising an anti-hCD3 antibody and an anti-hCD28 antibody;
    culturing the cells for a predetermined period of time, transfecting the cells with a CAR virus and the pLenti-CRISPRV2-sgRNA virus produced in Step 1, and expanding the transfected cells with stimulation; and
    removing CD3-positive cells from the obtained cells to get the CD3-negative CAR-T cells.

In some embodiments, wherein the lentiviral packaging plasmid in Step 1 comprises VSV-g, pMD Gag/Pol and RSV-REV In some embodiments, the centrifugation in Step 1 is performed using an ultracentrifuge and a head.

In some embodiments, the stimulation in Step 2 is performed stimulating with artificial antigen-presenting cells every 6 days or stimulating with anti-hCD3/anti-hCD28 every 6 days.

In some embodiments, the mononuclear cell is human mononuclear cell.

In some embodiments, the mononuclear cell is derived from cord blood or adult peripheral blood.

In some embodiments, said method further comprises the following step: performing herpes simplex virus thymidine kinase (HSV-TK) gene modification in a T cell.

The present disclosure further provides a formulation comprising the universal CAR-T cell of the present disclosure.

In some embodiments, the formulation comprises a pharmaceutically acceptable diluent or excipient.

The present disclosure further provides a use of the universal CAR-T cell of the present disclosure in preparation of a drug for treating and/or preventing tumor.

In some embodiments, the tumor comprises a solid tumor or a non-solid tumor.

In some embodiments, the solid tumor is selected from the group consisting of: lung cancer, breast cancer, colon cancer, renal cell carcinoma, liver cancer, non-small cell lung cancer, small intestine cancer, esophagus cancer, osteosarcoma, pancreatic cancer, skin cancer, head or neck cancer, cutaneous or intraocular malignant melanoma, uterus cancer, ovarian cancer, rectal cancer, anal cancer, stomach cancer, testis cancer, fallopian tube carcinoma, endometrial cancer, cervical cancer, vaginal cancer, vulval cancer, Hodgkin's disease, non-Hodgkin's lymphoma, carcinoma of endocrine system, thyroid cancer, parathyroid cancer, adrenal carcinoma, soft tissue sarcoma, urethral carcinoma, carcinoma of penis, pediatric solid tumor, bladder cancer, renal or ureteral cancer, carcinoma of renal pelvis, central nervous system (CNS) tumor, primary CNS lymphoma, tumor angiogenesis, spinal tumor, brainstem glioma, pituitary adenoma, Kaposi sarcoma, epidermoid, squamous cell carcinoma, and T cell lymphoma.

In some embodiments, the non-solid tumor is selected from the group consisting of chronic lymphoblastic leukemia (CLL), acute leukemia, acute lymphoblastic leukemia (ALL), B cell acute lymphoblastic leukemia (B-ALL), T cell acute lymphoblastic leukemia (T-ALL), chronic myeloid leukemia (CML), acute myeloid leukemia (AML), B cell prolymphocytic leukemia, blast cell plasmacytoid dendritic cytoma, Burkitt's lymphoma, diffuse large B cell lymphoma, follicular lymphoma, hairy cell leukemia, small or large cell follicular lymphoma, malignant lymphoproliferative conditions, MALT lymphoma, mantle cell lymphoma, marginal zone lymphoma, multiple myeloma, myelodysplasia and myelodysplastic syndrome, Hodgkin's lymphoma, plasmablast lymphoma, Plasmacytoid dendritic cytoma, B lymphocytoma, and Waldenstrom macroglobulinemia.

In some embodiments, wherein the tumor includes, but is not limited to, lymphoma, renal tumor, neuroblastoma, germ cell tumor, osteosarcoma, chondrosarcoma, soft tissue sarcoma, liver tumor, thymoma, pulmonary blastoma, pancreatoblastoma, hemangioma, etc.

The present disclosure further provides a method of treating tumor, including administering the universal CAR-T cell of the present application to a subject.

The present invention utilizes CRISPR/Cas9 to knock out CD3 (CD3Delta, CD3Gamma, CD3 Epsilon and/or CD3 zeta) to achieve an effect of avoiding GVHD, thereby constructing a universal CAR-T cell, improving the ease of use and scope of application of CAR-T cell therapy. At the same time, the present invention introduces the HSV-TK gene, thereby further improving the safety of universal CAR-T cell.

The universal CAR-T cell of the present invention exhibits a low graft-versus-host response (GVHD), and greatly enhances and expands the convenience of CAR-T cell therapy.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWING

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DETAILED DESCRIPTION

Figures 1A, 1B, 1C:
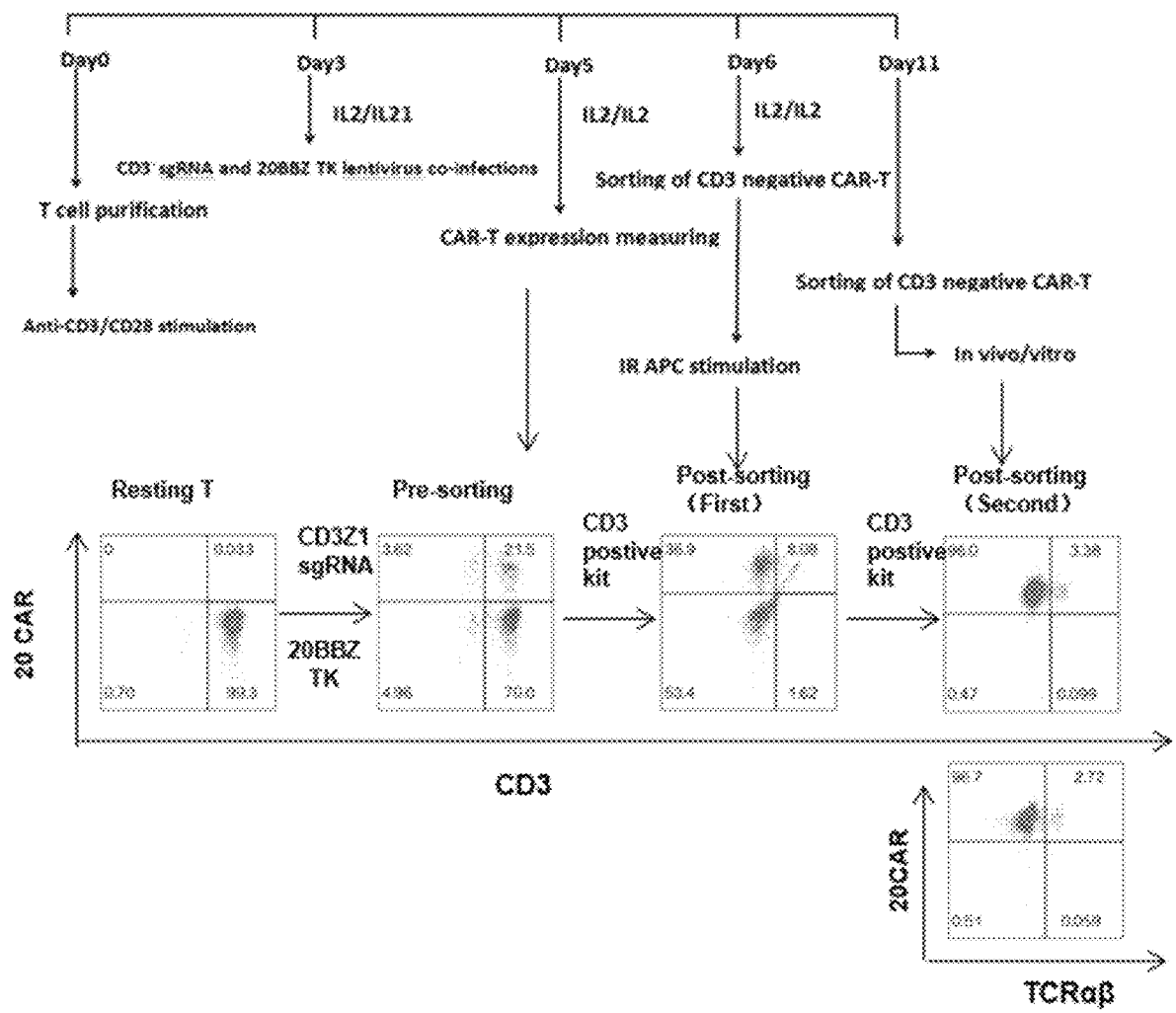
FIG. 1A illustrates schematic structural view of the BBZ CAR molecule.
FIG. 1B illustrates a schematic diagram of CD20 targeting CAR constructs. An anti-human CD20 scFv was linked to 41BB and CD3ζ, suicide gene thymidine kinase (TK) was linked to CD3ζ via a P2A sequence to generate a 20BBZ TK construct.
FIG. 1C illustrates Flow chart of the protocol to generate universal CAR-T (CD3-20uCAR-T) by 20BBZTK lentivirus and Cas9/gRNA lentivirus.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the term "CRISPR/Cas system" generally refers to a group of molecules including RNA-directed nuclease or other effector molecules and gRNA molecules, which can direct and realize the modification of nucleic acid at the site of targeting sequence by RNA-directed nuclease or other effector molecules, e.g., inducing degradation of the target sequence. In some embodiments, the CRISPR system includes gRNA and a Cas protein, e.g., a Cas9 protein. The system including Cas9 or a functional variant thereof is called "Cas9 system" or "CRISPR/Cas9 system" in the present application. In some embodiments, the gRNA molecule can be complexed with the Cas molecule to form a ribonucleoprotein (RNP) complex.

As used herein, the terms "gRNA molecule" or "guide RNA", "instruction RNA", "direct RNA", "guide RNA molecule", "gRNA" can be used interchangeably, and generally refer to a nucleic acid molecule that can promote directing the RNA-directed nuclease or other effector molecules (generally combined with gRNA molecules) specifically to the target sequence. In some embodiments, the directing is achieved by the hybridization of a portion of gRNA with DNA (e.g., via a gRNA guide domain) and the binding of a portion of gRNA molecule with an RNA directed nuclease or other effector molecules (e.g., at least through gRNAtracr). In some embodiments, the gRNA molecule consists of a single continuous polynucleotide molecule, which is herein referred to as a "single guide RNA" or "sgRNA" or the like. In other embodiments, the gRNA molecule consists of a plurality of (e.g., two) polynucleotide molecules that can be associated with themselves (generally by hybridization), which is herein referred to as "double guide RNA" or "dgRNA", etc.

As used herein, the term "Cas protein" generally refers to an enzyme responsible for cutting DNA in the CRISPR/Cas system. It can include enzymes from CRISPR/Cas system Types I, II, and III, e.g., Cas3, Cas9, Cas10.

As used herein, the term "Cas9 protein" generally refers to an enzyme from the bacterial type II CRISPR/Cas system and responsible for cutting DNA. Cas9 can include the wild-type protein and functional variants thereof.

As used herein, the term "chimeric antigen receptor (CAR)" generally refers to an antigen receptor fused by fusing an antigen binding region of an antibody which recognizes a tumor associated antigen (TAA) or a binding fragment of other target molecules with an "immune receptor tyrosine-based activation motifs (ITAM, typically CD3ζ or FcεRIγ) of an intracellular signal domain. For example, the basic structure of CAR can include an antigen binding domain of a tumor-associated antigen (TAA) or other target molecules (typically, an scFv originated from the antigen binding region of a monoclonal antibody), an extracellular hinge region, a transmembrane region, and an immunoreceptor tyrosine-based activation motif (ITAM) of an intracellular immune receptor.

As used herein, the term "binding domain" generally refers to a domain that (specifically) binds to a given target epitope or a given target site of a target molecule (e.g., an antigen), interacts with the given target epitope or the given target site, or recognizes the given target epitope or the given target site.

As used herein, the term "specific binding" generally refers to a measurable and reproducible interaction, such as, the binding between a target and an antibody, which can determine the presence of a target in the presence of heterogeneous populations of molecules (including biomolecules). For example, antibodies that specifically bind to targets (which can be epitopes) are antibodies that bind the target(s) with greater compatibility, affinity, easiness, and/or duration than other targets. In some embodiments, the antibody specifically binds to an epitope on a protein that is conserved in proteins of different species. In another embodiment, the specific binding includes but is not limited to exclusive binding.

As used herein, the term "transmembrane domain" generally refers to a polypeptide or protein which is encoded at a DNA level by an exon including at least an extracellular region, a transmembrane region, and an intracellular region.

The transmembrane domain generally includes three different structural regions: N-terminal extracellular region, middle conserved transmembrane extension region, and C-terminal cytoplasmic region. The transmembrane domain may further include an intracellular region or a cytoplasmic region.

As used herein, the term "hinge region" generally refers to a region located between the binding domain and the transmembrane domain in the CAR structure. The hinge region usually comes from IgG family, such as IgG1 and IgG4, and some from IgD and CD8. Generally, the hinge region has a certain degree of flexibility, which affects the spatial constraints between the CAR molecule and its specific target, thereby affecting the contact between CAR T cells and tumor cells.

As used herein, the term "costimulatory" generally refers to a source of the second signal of lymphocyte activation, which is usually generated by an interaction of costimulatory molecules on the surface of immune cells (between T cells/B cells or between antigen presenting cells/T cells) involved in adaptive immunity with their receptors. For example, the complete activation of T cells depends on dual signaling and the action of cytokine. The first signal of T cell activation is derived from the specific binding of its receptors with the antigens, that is, the recognition of T cells to the antigens; and the second signal of T cell activation is derived from the costimulatory molecule, that is, the interaction of the costimulatory molecules of the antigen presenting cells with the corresponding receptors on the surfaces of T cells.

As used herein, the term "costimulatory domain" generally refers to an intracellular portion of the corresponding receptor of the costimulatory molecule, which can transduce a costimulatory signal (also known as the second signal). For example, in CAR-T cells, the costimulatory domain derived from CD137 (or receptors of other costimulatory molecules) can be activated after the binding of the extracellular binding domain in the CAR structure with the corresponding antigen, thereby transducing a costimulatory signal.

As used herein, the term "primary signal transduction domain" generally refers to an amino acid sequence within a cell that can generate signals which promote the immune effector function of CAR-containing cells such as CAR-T cells. Examples of the immune effector functions in, e.g., CAR-T cells can include cell lysis activity and auxiliary activity, including cytokine secretion. In some embodiments, the primary signal transduction domain transduces the effector functional signals and directs the cells to perform the specialization function. Although the primary signal transduction domain can be used in its entirety, it is not necessary to use the entire chain in many cases. As for the use of a truncated portion of the primary signal transduction domain, such truncated portion can be used to replace the intact chain, as long as it can transduce the effector functional signals. The term "primary signal transduction domain" is thus intended to encompass any truncated portion of an intracellular signal transduction domain that is sufficient to transduce the effector functional signals.

As used herein, the term "tumor" generally refers to a neoplasm or solid lesion formed by abnormal cell growth. In the present application, the tumor can be a solid tumor or a non-solid tumor. In some embodiments, a visible lump that can be detected by clinical examinations such as, X-ray radiography, CT scanning, B-ultrasound or palpation can be called solid tumor, while a tumor that cannot be seen or touched by X-ray, CT scanning, B-ultrasound and palpation, such as leukemia, can be called non-solid tumor.

As used herein, the term "pharmaceutically acceptable diluent" or "pharmaceutically acceptable excipient" generally refers to a pharmaceutically acceptable substance, composition, or vehicle involved in carrying, storing, transferring, or administering a cell preparation, e.g., liquids, semi-solid or solid fillers, diluents, osmotic agents, solvent, or encapsulating substances. The pharmaceutically acceptable diluent or excipient can include a pharmaceutically acceptable salt, wherein the term "pharmaceutically acceptable salt" includes salts of active compounds prepared by using a relatively nontoxic acid or base, e.g., sodium chloride, depending on the cell nature of the present application. The pharmaceutically acceptable carrier can further include organic acids (e.g., lactic acid), bioactive substances (e.g., polypeptides, antibodies, and the like) and antibiotics (e.g., penicillin, streptomycin), etc. The pharmaceutically acceptable carrier can further include a hydrogel, such as, a hydrogel containing polyacrylamide. The pharmaceutically acceptable diluent or excipient can include storage solution, cryopreservation solution, injection, etc., which can be used for cells. In general, the pharmaceutically acceptable diluent or excipient can maintain the activity of the cells carried by the carrier without hindering its therapeutic efficacy. The pharmaceutically acceptable diluent or excipient can also contribute to the storage, transportation, proliferation and migration of cells, and is suitable for clinical application.

As used herein, the term "allogeneic therapy" generally refers to a therapy of administering organs, tissues, cells, etc. which do not come from the subject or patient to achieve a therapeutic purpose.

As used herein, the term "subject" generally refers to a human or non-human animal, including but not limited to a cat, dog, horse, pig, cow, sheep, rabbit, mouse, rat, or monkey. In some embodiments, said subject is a human.

As used herein, the term "include/including" or "comprise/comprising" generally refers to encompassing clearly specified features, but does not exclude other elements.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Preparation of CD3-Negative 20BBZ CAR-T Cells 1.1 Construction of Lentiviral Vector pLenti-CrisprV2-sgRNA and Production of Virus A sgRNA for CD3Delta, CD3Gamma, CD3 Epsilon, CD3 zeta is designed by using crispr.mit.edu (Table 1), and cloned into pLenti-CrisprV2.

The correctly sequenced clones were extracted with the "endotoxin removal" kit, and pLenti-CrisprV2 containing different clones (KO CD3Delta sgRNA, KO CD3Gamma sgRNA, KO CD3 Epsilon sgRNA or KO CD3 zeta sgRNA) and lentivirus packaging plasmids (VSV-g, pMD Gag/Pol and RSV-REV) were co-transfected with 293X, supernatants were collected after 48 and 72 hours, filtered at 0.45 uM and the viruses were concentrated by centrifugation at 25,000 RPM for 2 hours using a Beckman ultracentrifuge and SW28 head to obtain plenti-CRISPRV2-sgRNA viruses for subsequent CAR-T cell production.

TABLE 1

| LABEL | SEQ | SEQ ID NO: |
|---|---|---|
| KO CD3Delta sgRNA1 (D1) | GAACATAGCACGTTTCTCTC | 1 |
| KO CD3Delta sgRNA2 (D2) | CCCCTTCAAGATACCTATAG | 2 |
| KO CD3Gamma sgRNA1 (G1) | GGCTATCATTCTTCTTCAAG | 3 |
| KO CD3Gamma sgRNA2 (G2) | CTTGGTTAAGGTGTATGACT | 4 |
| KO CD3Gamma sgRNA3 (G3) | GTAATGCCAAGGACCCTCGA | 5 |
| KO CD3 Epsilon sgRNA1 (E1) | GGGCACTCACTGGAGAGTTC | 6 |
| KO CD3 Epsilon sgRNA2 (E2) | TTGACATGCCCTCAGTATCC | 7 |
| KO CD3 zeta sgRNA1 (Z1) | GTGGAAGGCGCTTTTCACCG | 8 |
| KO CD3 zeta sgRNA2 (Z2) | TTTCACCGCGGCCATCCTGC | 9 |
| KO CD3 zeta sgRNA3 (Z3) | GATGGAATCCTCTTCATCTA | 10 |

1.2 sgRNA Knockdown Efficiency Assay $2 \times 10^5$ Jurkat cells were transiently transfected with 0.6 μg pLenti-CrisprV2-hCD3E1/E2/D1/D2/Z1/Z2/G1/G2/G3 plasmids and cells were harvested at 48 h. Anti-TCR antibody was used for flow detection and untransfected plasmids were used as negative control.

Figure 1D:
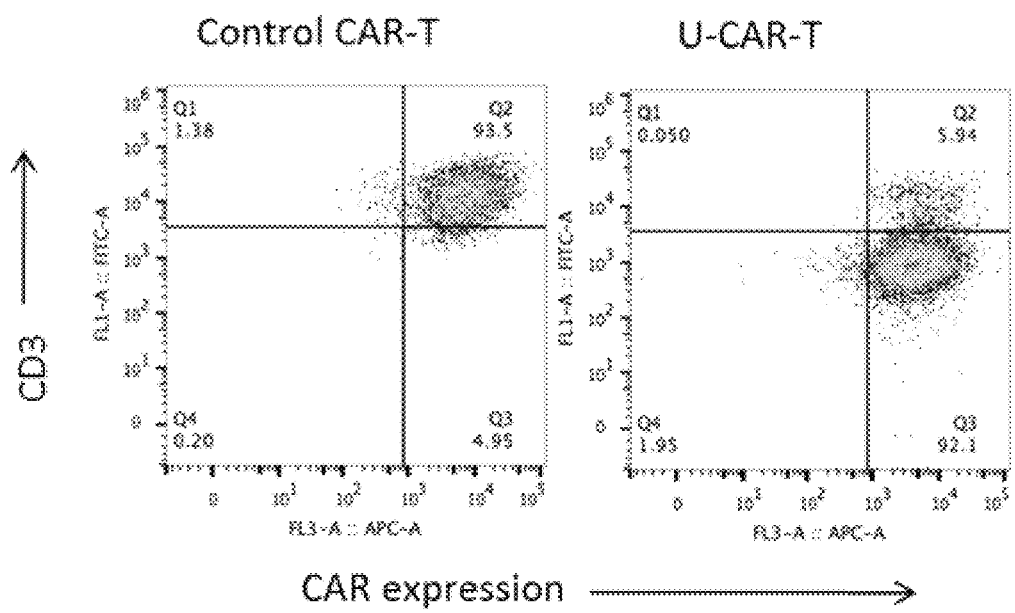
FIG. 1D illustrates schematic view of the results of the phenotypic analysis of the CD3-negative 20BBZ CAR-T cells.
Figure 1E:
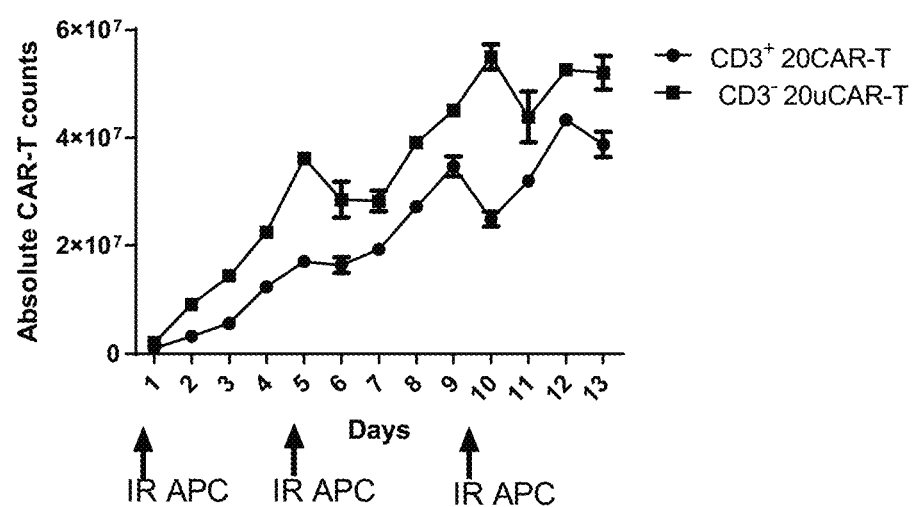
FIG. 1E illustrates schematic diagram of long-term CAR-T population expansion.
Figure 1F:
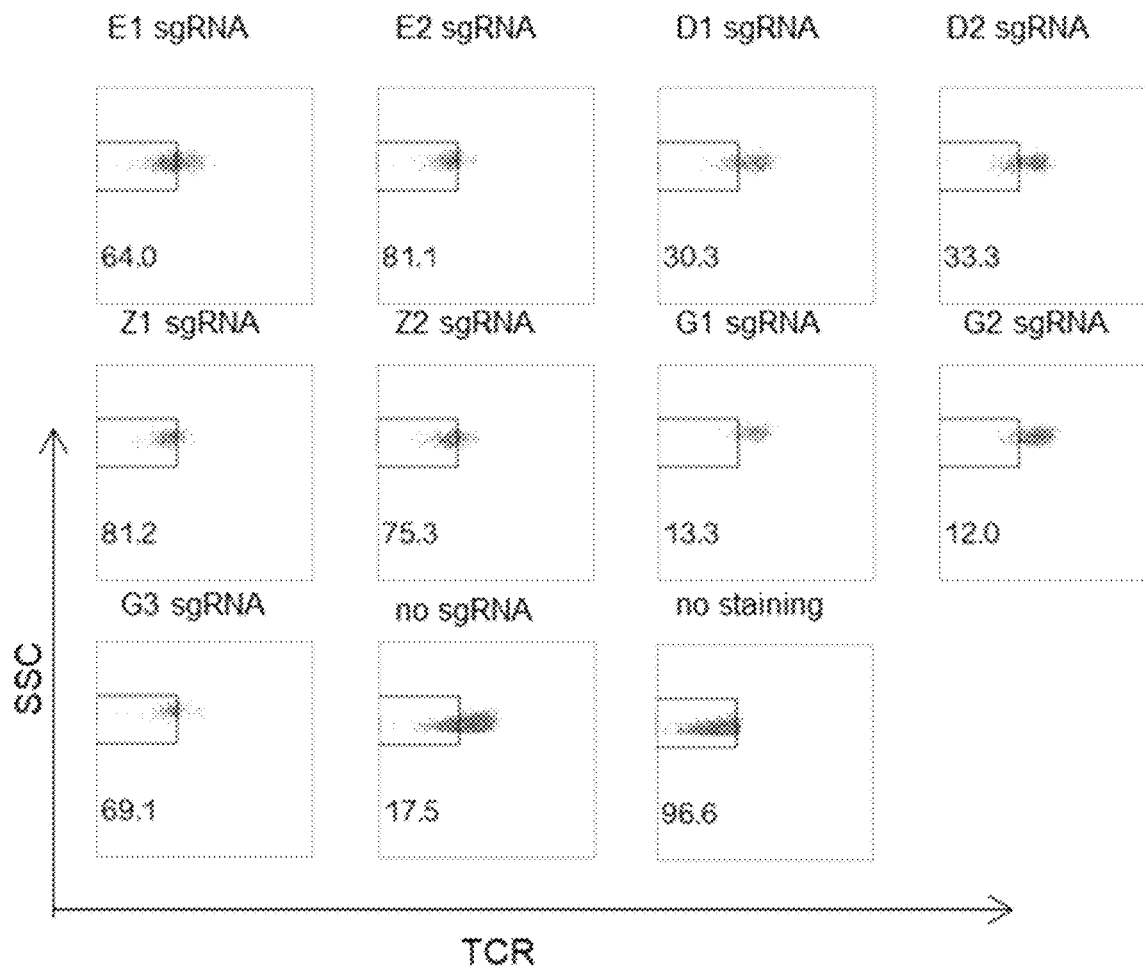
FIG. 1F illustrates the knockout efficiency of sgRNA of on CD3 gene.

FIG. 1F showed that CD3 is not expressed when the corresponding sequence is knocked down with sgRNA. The box in the figure represented the knockdown efficiency, where Z1 has the highest knockdown efficiency (about 81.2%).

1.3 Construction of 20BBZ CAR

The BBZ (its structure was shown in FIG. 1A, and the antibody extracellular antigen recognition domain used therein is anti-CD20 antibody), HSV-TK was added to its middle by overlap PCR to form the gene encoding the fusion protein, and the lentiviral vector was cloned by adding the enzyme cut site at both ends; the correctly sequenced clones were extracted with the "endotoxin removal" kit, and the lentiviral packaging plasmid were co-transfected, and the supernatant was collected at a predetermined time, and the virus was concentrated by filtration and centrifugation to obtain the 20BBZ-2A-TK (its structure was shown in FIG. 1B, and the sequence is shown in Table 2) virus.

The 19BBZ CAR (the sequence is shown in Table 2) can also be constructed according to the above method.

TABLE 2

| LABEL | SEQ | SEQ ID NO: |
|---|---|---|
| anti-CD20 scFv | QIVLSQSPAILSASPGEKVTMTCRASSSVSYIHWFQQKPGSSPKPW IYATSNLASGVPVRFSGSGSGTSYSLTISRVEAE DAATYYCQQWTSNPPTFGGGTKLEIKGGGGSGGGGSGG GGSQVQLQQPGAELVKPGASVKMSCKASGYTFTSYNM HWVKQTPGRGLEWIGAIYPGNGDTSYNQKFKGKATLTA DKSSSTAYMQLSSLTSEDSAVYYCARSTYYGGDWYFNV WGAGTTVTVS | 11 |
| CD8a Hinge | TTTPAPRPPTPAPTIASQPLSLRPEACRPAAGGAVHTRGL DFACD | 12 |
| CD8a transmembrane domain | IYIWAPLAGTCGVLLLSLVITLYC | 13 |
| 4-1BB | KRGRKKLLYIFKQPFMRPVQTTQEEDGCSCRFPEEEEGG CEL | 14 |
| CD3zeta | RVKFSRSADAPAYQQGQNQLYNELNLGRREEYDVLDK RRGRDPEMGGKPRRKNPQEGLYNELQKDKMAEAYSEIG MKGERRRGKGHDGLYQGLSTATKDTYDALHMQALPPR | 15 |
| the kappa leader sequence | METDTLLLWVLLLWVPGSTGTG | 16 |

TABLE 2-continued

| LABEL | SEQ | SEQ ID NO: |
|---|---|---|
| 2A | GSGATNFSLLKQAGDVEENPGP | 19 |
| TK | MASYPCHQHASAFDQAARSRGHSNRRTALRPRRQQEAT EVRLEQKMPTLLRVYIDGPHGMGKTTTTQLLVALGSRD DIVYVPEPMTYWQVLGASETIANIYTTQHRLDQGEISAG DAAVVMTSAQITMGMPYAVTDAVLAPHVGGEAGSSHA PPPALTLIFDRHPIAALLCYPAARYLMGSMTPQAVLAFV ALIPPTLPGTNIVLGALPEDRHIDRLAKRQRPGERLDLAM LAAIRRVYGLLANTVRYLQGGGSWWEDWGQLSGTAVP PQGAEPQSNAGPRPHIGDTLFTLFRAPELLAPNGDLYNV FAWALDVLAKRLRPMHVFILDYDQSPAGCRDALLQLTS GMVQTHVTTPGSIPTICDLARTFAREMGEAN | 20 |
| 20BBZ-2A-TK (anti-CD20 scFv-hinge-TM-41BBICD-CD3Z-2A-TK) | METDTLLLWVLLLWVPGSTGTGQIVLSQSPAILSASPGE KVTMTCRASSSVSYIHWFQQKPGSSPKPWIYATSNLASG VPVRFSGSGSGTSYSLTISRVEAEDAATYYCQQWTSNPP TFGGGTKLEIKGGGGSGGGGSGGGGSQVQLQQPGAELV KPGASVKMSCKASGYTFTSYNMHWVKQTPGRGLEWIG AIYPGNGDTSYNQKFKGKATLTADKSSSTAYMQLSSLTS EDSAVYYCARSTYYGGDWYFNVWGAGTTVTVSAAAA TTTPAPRPPTPAPTIASQPLSLRPEACRPAAGGAVHTRGL DFACDIYIWAPLAGTCGVLLLSLVITLYCKRGRKKLLYIF KQPFMRPVQTTQEEDGCSCRFPEEEEGGCELRVKFSRSA DAPAYQQGQNQLYNELNLGRREEYDVLDKRRGRDPEM GGKPRRKNPQEGLYNELQKDKMAEAYSEIGMKGERRR GKGHDGLYQGLSTATKDTYDALHMQALPPRGSGATNFS LLKQAGDVEENPGPRTMASYPCHQHASAFDQAARSRGH SNRRTALRPRRQQEATEVRLEQKMPTLLRVYIDGPHGM GKTTTTQLLVALGSRDDIVYVPEPMTYWQVLGASETIA NIYTTQHRLDQGEISAGDAAVVMTSAQITMGMPYAVTD AVLAPHVGGEAGSSHAPPPALTLIFDRHPIAALLCYPAAR YLMGSMTPQAVLAFVALIPPTLPGTNIVLGALPEDRHIDR LAKRQRPGERLDLAMLAAIRRVYGLLANTVRYLQGGGS WWEDWGQLSGTAVPPQGAEPQSNAGPRPHIGDTLFTLF RAPELLAPNGDLYNVFAWALDVLAKRLRPMHVFILDYD QSPAGCRDALLQLTSGMVQTHVTTPGSIPTICDLARTFA REMGEAN | 21 |
| anti-CD19 scFv | DIQMTQTTSSLSASLGDRVTISCRASQDISKYLNWYQQK PDGTVKLLIYHTSRLHSGVPSRFSGSGSGTDYSLTISNLE QEDIATYFCQQGNTLPYTFGGGTKLEITGGGGSGGGGS GGGSEVKLQESGPGLVAPSQSLSVTCTVSGVSLPDYGVS WIRQPPRKGLEWLGVIWGSETTYYNSALKSRLTIIKDNS KSQVFLKMNSLQTDDTAIYYCAKHYYYGGSYAMDYW GQGTSVTVSS | 24 |
| 19BBZ-2A-TK (anti-CD19 scFv-hinge-TM-41BBICD-CD3Z-2A-TK) | METDTLLLWVLLLWVPGSTGTGDIQMTQTTSSLSASLG DRVTISCRASQDISKYLNWYQQKPDGTVKLLIYHTSRLH SGVPSRFSGSGSGTDYSLTISNLEQEDIATYFCQQGNTLP YTFGGGTKLEITGGGGSGGGGSGGGSEVKLQESGPGL VAPSQSLSVTCTVSGVSLPDYGVSWIRQPPRKGLEWLGV IWGSETTYYNSALKSRLTIIKDNSKSQVFLKMNSLQTDD TAIYYCAKHYYYGGSYAMDYWGQGTSVTVSSAAAATT TPAPRPPTPAPTIASQPLSLRPEACRPAAGGAVHTRGLDF ACDIYIWAPLAGTCGVLLLSLVITLYCKRGRKKLLYIFKQ PFMRPVQTTQEEDGCSCRFPEEEEGGCELRVKFSRSADA PAYQQGQNQLYNELNLGRREEYDVLDKRRGRDPEMGG KPRRKNPQEGLYNELQKDKMAEAYSEIGMKGERRRGK GHDGLYQGLSTATKDTYDALHMQALPPRGSGATNFSLL KQAGDVEENPGPRTMASYPCHQHASAFDQAARSRGHS NRRTALRPRRQQEATEVRLEQKMPTLLRVYIDGPHGMG KTTTTQLLVALGSRDDIVYVPEPMTYWQVLGASETIANI YTTQHRLDQGEISAGDAAVVMTSAQITMGMPYAVTDA VLAPHVGGEAGSSHAPPPALTLIFDRHPIAALLCYPAARY LMGSMTPQAVLAFVALIPPTLPGTNIVLGALPEDRHIDRL AKRQRPGERLDLAMLAAIRRVYGLLANTVRYLQGGGS WWEDWGQLSGTAVPPQGAEPQSNAGPRPHIGDTLFTLF RAPELLAPNGDLYNVFAWALDVLAKRLRPMHVFILDYD QSPAGCRDALLQLTSGMVQTHVTTPGSIPTICDLARTFA REMGEAN | 26 |

1.4 Preparation of CD3-Negative 20BBZ CAR-T Cells

Human PBMC were purified by Stemcell T cell isolation kit (negative selection) and inoculated into anti-hCD3 and anti-hCD28-coated 96-well culture plates, and after 2 days, the cells were infected with 20BBZ-2A-TK virus according to MOI=10-20 and pLentiCRISPRv2-hCD3Z1 virus, the cell culture was continued with the medium changed after 1 day, and artificial antigen-presenting cells were used according to every 6 days, and the cells were removed from CD3-positive cells with the Stemcell T cell positive selection kit, i.e., CD3-negative 20BBZ CAR-T cells (CD3-U-CAR-T, referred to as U-CAR-T cells) were obtained for subsequent experiments and phenotypic analysis were shown in FIG. 1D. As can be seen from the figure, the resulting U-CAR-T cells were CAR-positive and CD3-negative.

1.5 The Characteristic of CD3− 20uCAR-T

T cells were infected with 20BBZ TK lentivirus and electroporated with Cas9/gRNA which stimulated by coculture with irradiated (IR) Raji cells once every 6 days. The characteristic of CD3+20CAR-T and CD3−20uCAR-T were analyzed on day 4 after each stimulation. Overall expansion of CAR-T cells in CD3+20CAR-T and CD3−20uCAR-T. Relative cell proliferation was calculated by dividing the cell number of Day 1. Experiments were repeated with four different donor-derived T cells (n=4/group). Arrows indicate stimulation time point.

FIG. 1E shows that CAR-T cell expansion was not significantly affected by knockdown of CD3 and still had good amplification.

Example 2 The Cytotoxicity of CD3− 20uCAR-T In Vitro

Figure 2A:
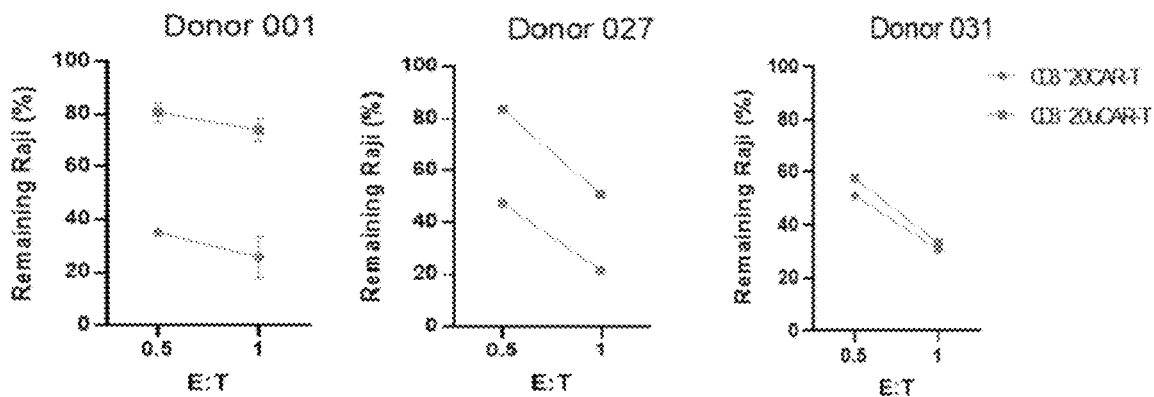
FIG. 2A illustrates the relative cytotoxicity of CD3⁻20uCAR-T by analyzing the remaining tumor cells (CD19⁺) by flow cytometry.
Figure 2B:
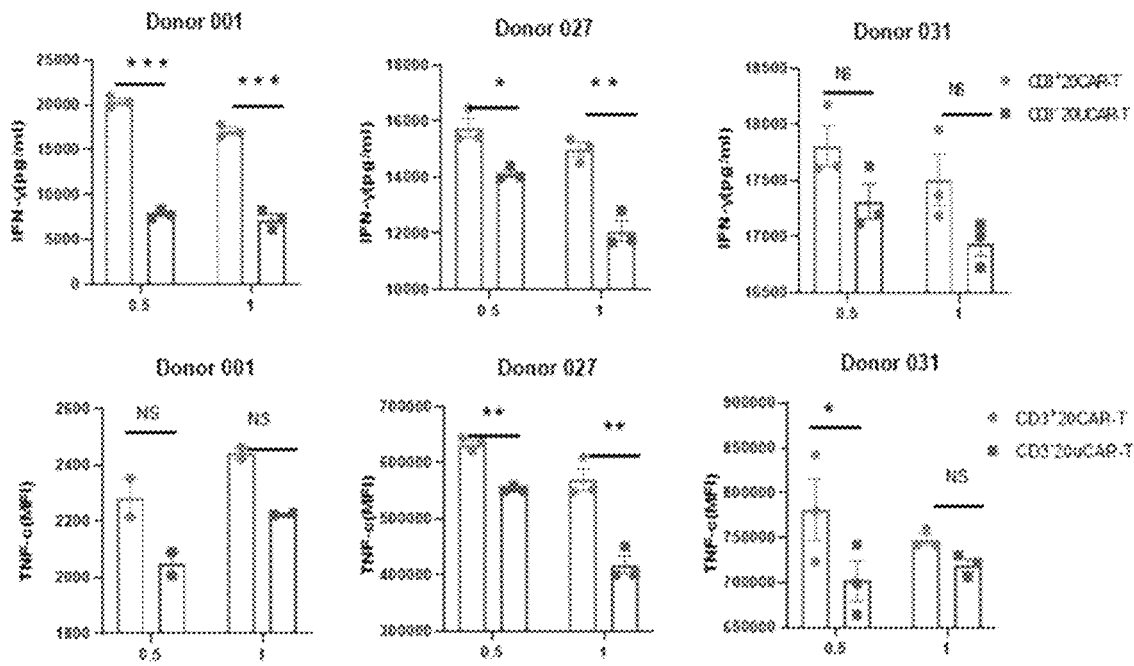
FIG. 2B illustrates cytokines IFN-γ and TNF-α secreted by CD3⁺20CAR-T and CD3⁻20uCAR-T cells.

CD3+20CAR-T and CD3−20uCAR-T cells constructed from three different donor were co-culture with Raji cells at the different effector:target (E:T) ratio for 24 h. Relative cytotoxicity was calculated by analyzing the remaining tumor cells (CD19+) by flow cytometry. Cytokines IFN-γ and TNF-α secreted by CD3+20CAR-T and CD3−20uCAR-T cells were determined by Cytometric Bead Array (CBA) assay. Representative results of one from three (FIG. 2A-2B) repeated experiment are shown. *P<0.05, P<0.01, *P<0.001; NS: Not Significant FIG. 2A-2B show that after knockdown of CD3, CD3− UCAR-T still had promising tumor killing effect as well as a higher level of cytokine (IFN-γ, TNF-α) secretion.

Example 3 CD3−20u CAR-T Cells Show Better Effectively Controlling Tumor In Vivo

NSG mice (n=6/group) were intravenously inoculated with 5×10$^5$ Raji (FIG. 3B) or daudi (FIG. 3C) tumor cell. Seven days later, tumor bearing mice were treated with 1×10$^7$ CD3+20CAR-T cells or CD3−20uCAR-T cells or PBS. Kaplan-Meier curves for overall survival of the mice are shown. Statistical significance was determined by Mantel-Cox test, presented P<0.01, *P<0.001; NS: Not Significant.

Figure 3A:
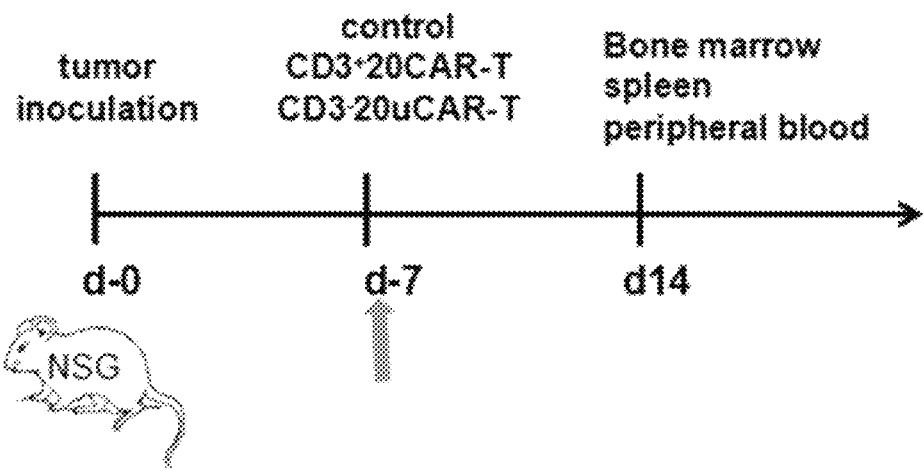
FIG. 3A illustrates a schematic diagram of the in vivo xenograft tumor model and CAR-T treatment protocol.
Figure 3B:
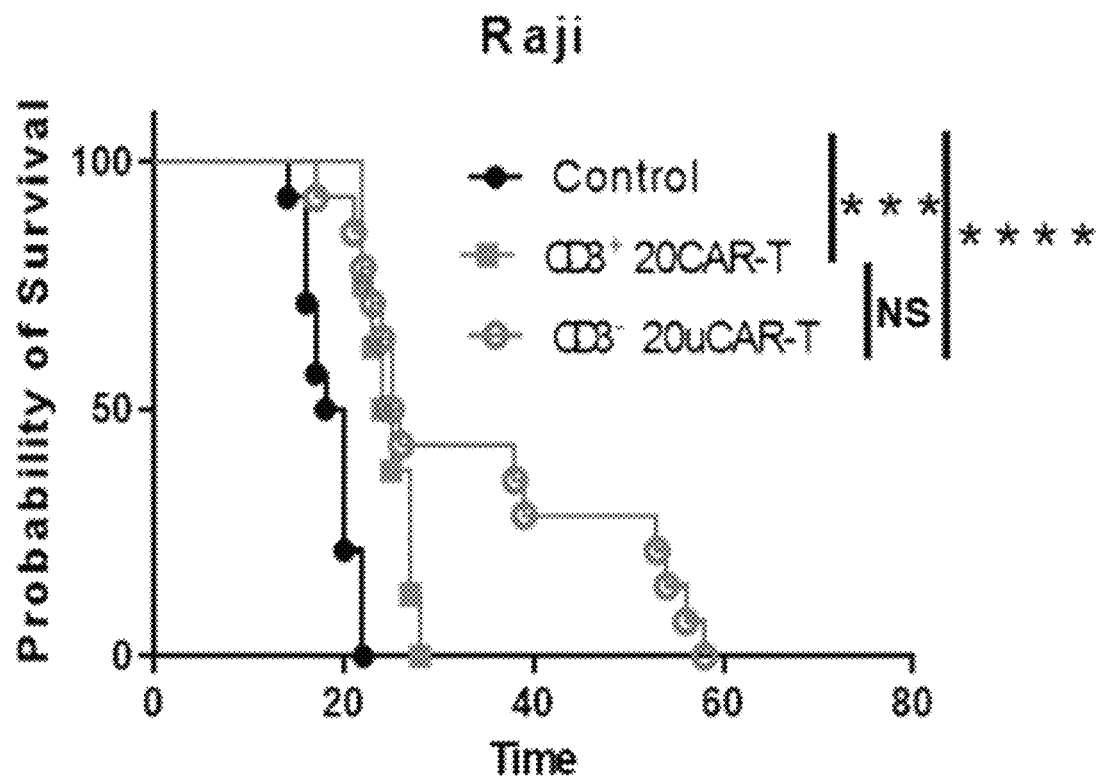
FIG. 3B-3C illustrate Kaplan-Meier curves for overall survival of the mice.
Figure 3C:
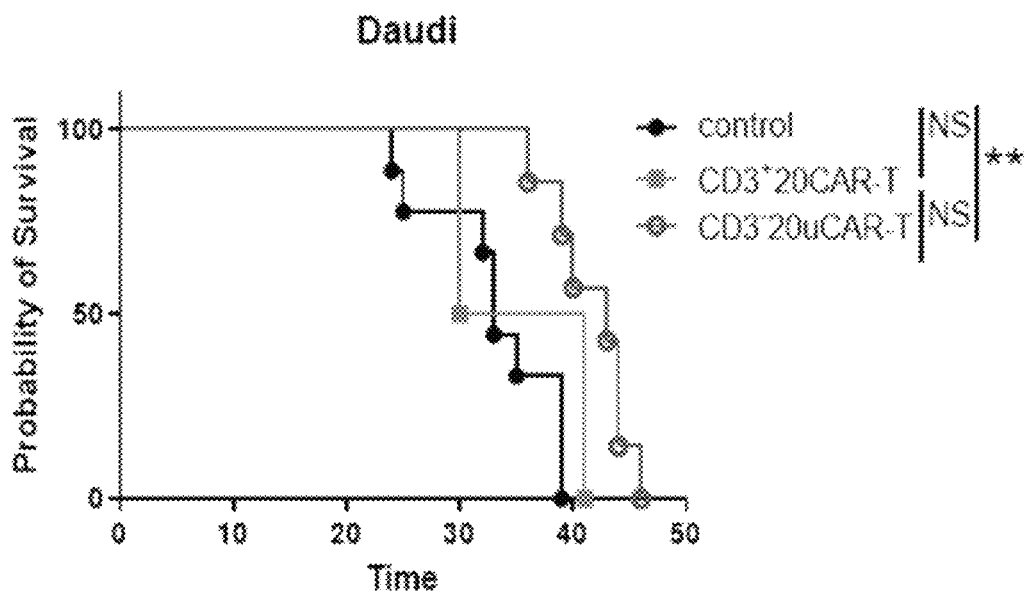
Figure 3D:
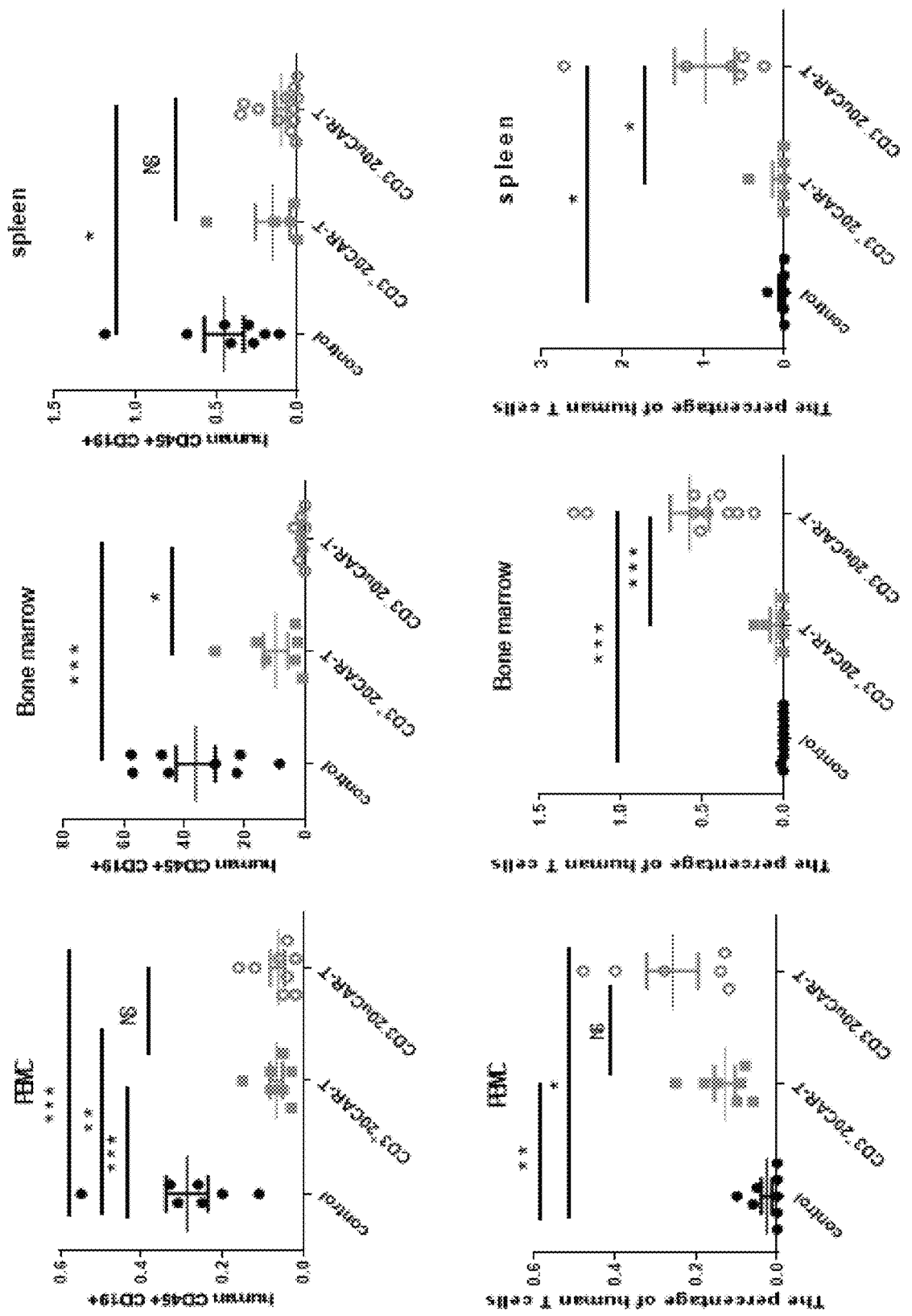
FIG. 3D illustrates analysis of CAR-T cell (mCD45⁻hCD45⁺hCD3⁺) persistence and Raji (mCD45⁻hCD45⁺hCD19⁺) tumor cell burden

Same as in FIG. 3B, 7 days after the treatment, bone marrow, spleen and peripheral blood were collected for analysis of CAR-T cell (mCD45−hCD45+hCD3+) persistence and Raji (mCD45−hCD45+hCD19+) tumor cell burden (FIG. 3D). Statistical significance was determined by Mann-Whitney U test and presented by *P<0.05, P<0.01, *P<0.001; NS: Not Significant.

FIG. 3D shows that CD3-CAR-T has a lower tumor cell burden and higher CAR-T cell persistence compared to control or CD3+ CAR-T, indicating that CD3-UCAR-T has better efficacy.

Figure 4A:
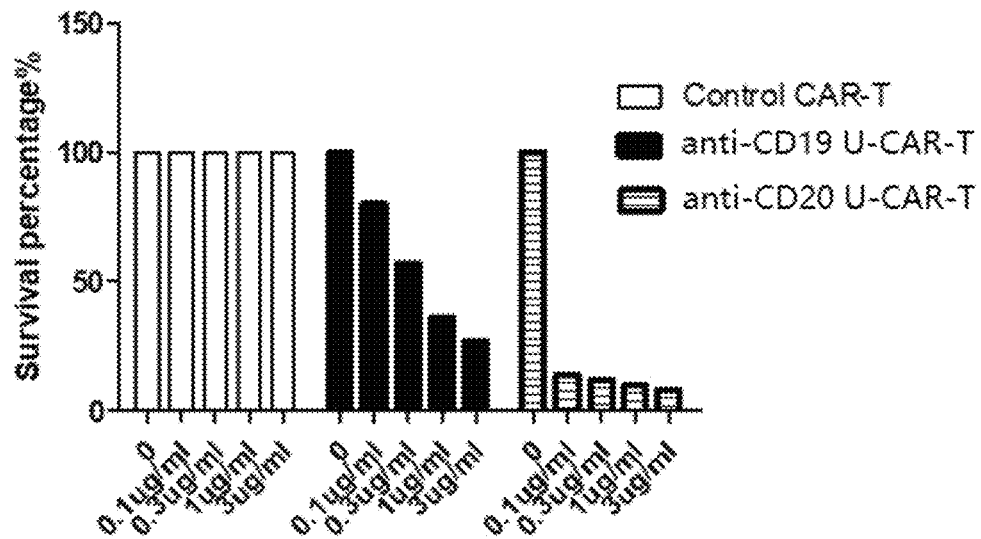
FIG. 4A illustrates schematic view showing the regulation of ganciclovir on the survival of the CD3-negative 20BBZ CAR-T cells and the CD3-negative 19BBZ CAR-T cells in vitro.
Figure 4B:
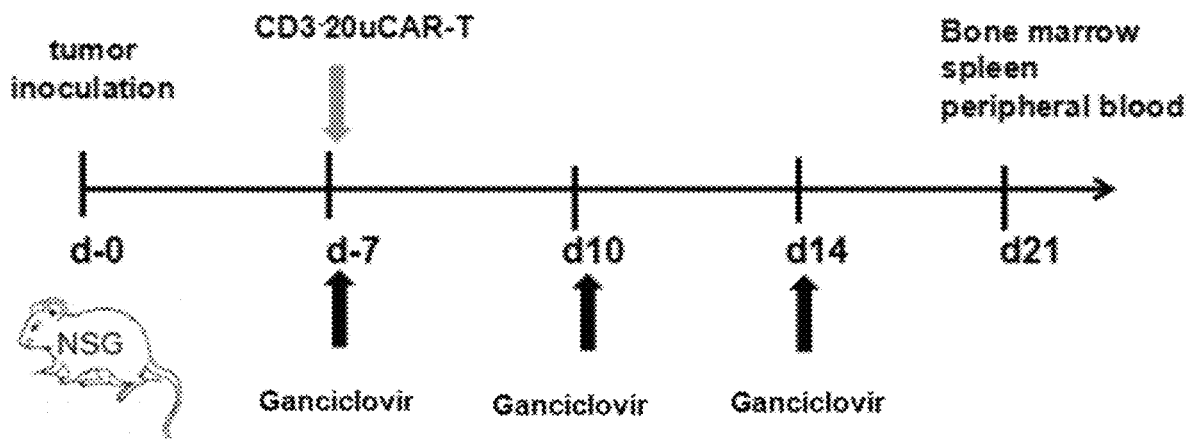
FIG. 4B illustrates a schematic diagram of the in vivo xenograft tumor model and CAR-T treatment protocol.

Example 4 the Survival of U-CAR-T Cell is Regulated by Ganciclovir 4.1 the Survival of U-CAR-T Cell is Regulated by Ganciclovir In Vitro The anti-CD20 U-CAR-T cells obtained in Example 1, anti-CD19 U-CAR-T cells (prepared according to the method in Example 1) and the control CAR-T (without knockout of CD3) were inoculated into 96-well plates, and the number of surviving CAR-Ts was compared after 48 hours by adding the indicated concentration of ganciclovir (0, 0.1 μg/mL, 0.3 μg/mL, 1 μg/mL, 3 μg/mL), and the results are shown in FIG. 4A. From the figure, it can be seen that ganciclovir can regulate the survival of U-CAR-T, which can rapidly remove U-CAR-T from the body under the condition that U-CAR-T causes side effects and improves safety.

4.2 the Survival of U-CAR-T Cell is Regulated by Ganciclovir In Vivo

Figure 4C:
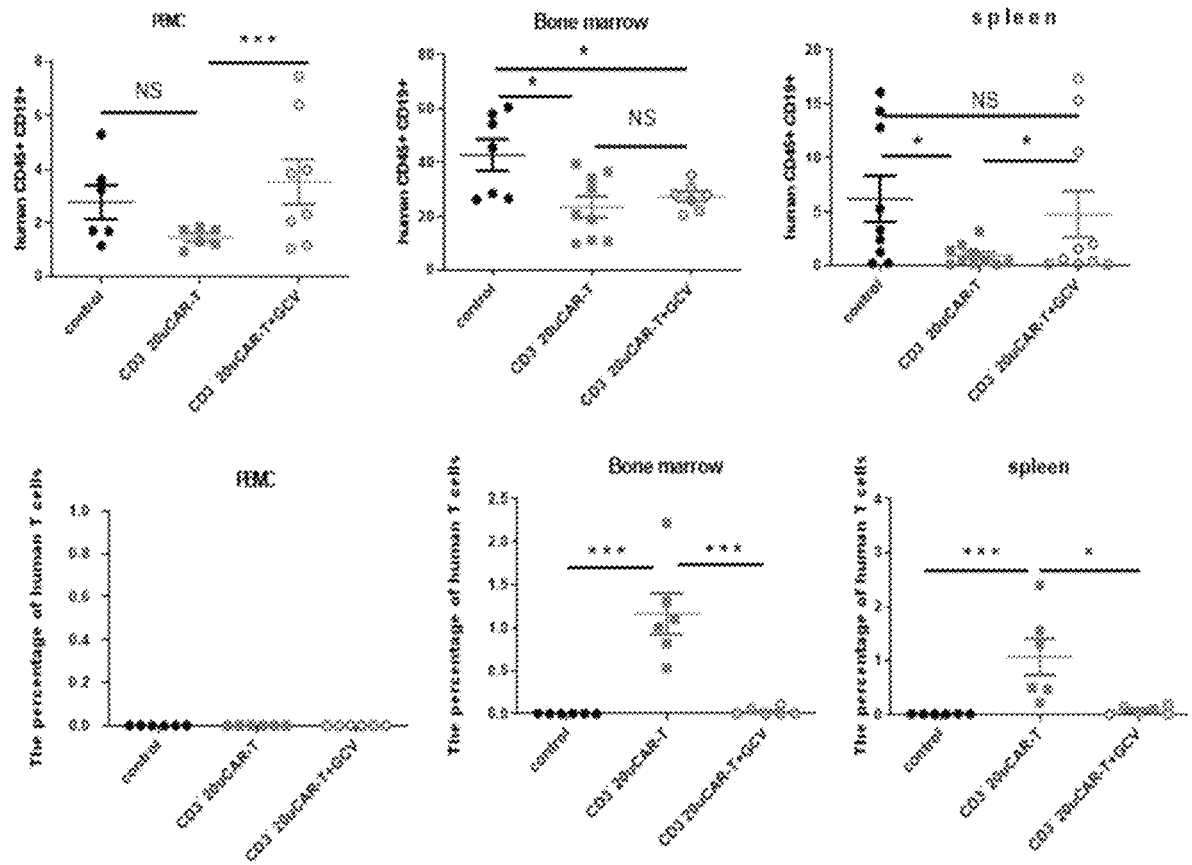
FIG. 4C illustrates analysis of CAR-T cell (mCD45⁻hCD45⁺hCD3⁺) persistence and Raji (mCD45⁻hCD45⁺hCD19⁺) tumor cell burden.

NSG mice (n=6/group) were injected intravenously with 5×10$^5$ Raji, which was followed by the administration of 1×10$^7$ CD3−20uCAR-T cells on day 7 or two hundred micrograms of Ganciclovir were administered on day 7, 10 and 13. 7 days after the treatment, bone marrow, spleen and peripheral blood were collected for analysis of CAR-T cell (mCD45−hCD45+hCD3+) persistence and Raji (mCD45−hCD45+hCD19+) tumor cell burden (FIG. 4C). Statistical significance was determined by Mann-Whitney U test and presented by *P<0.05, P<0.01, *P<0.001; NS: Not Significant. Statistical significance was determined by unpaired t test. Statistical significance was presented by *P<0.05, ***P<0.001.

FIG. 4C shows that ganciclovir effectively cleared CD3− UCAR-T cells from various organs in vivo compared to CD3+ CAR-T (control is a group without CAR-T cells). As CD3− UCAR-T cells were cleared, there was an elevated tumor load compared to CD3+ CAR-T.

Example 5 Comparison of Tumor-Killing Ability of U-CAR-T and Control CAR-T

Figure 5:
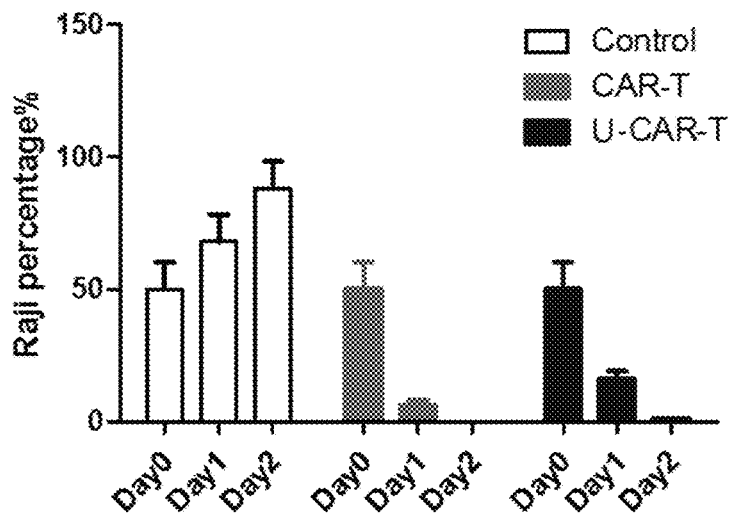
FIG. 5 illustrates schematic view of the tumor-killing ability of the CD3-negative 20BBZ CAR-T cells and the control CAR-T cells in an embodiment of the present invention.

The anti-CD20 U-CAR-T cells obtained in EXAMPLE 1 and the control CAR-T cells (without knockout of CD3) were inoculated into 96-well plates, and Raji tumor cells were added at a CAR-T:tumor cells ratio of 1:1. After 24 and 48 hours, the survival rates of the tumor cells were compared, and the results are shown in FIG. 5. It can be seen from the figure that the U-CAR-T has a similar tumor killing ability to that of the control CAR-T.

Example 6 Comparison of In Vivo Survival Ability of U-CAR-T and Control CAR-T

Figure 6:
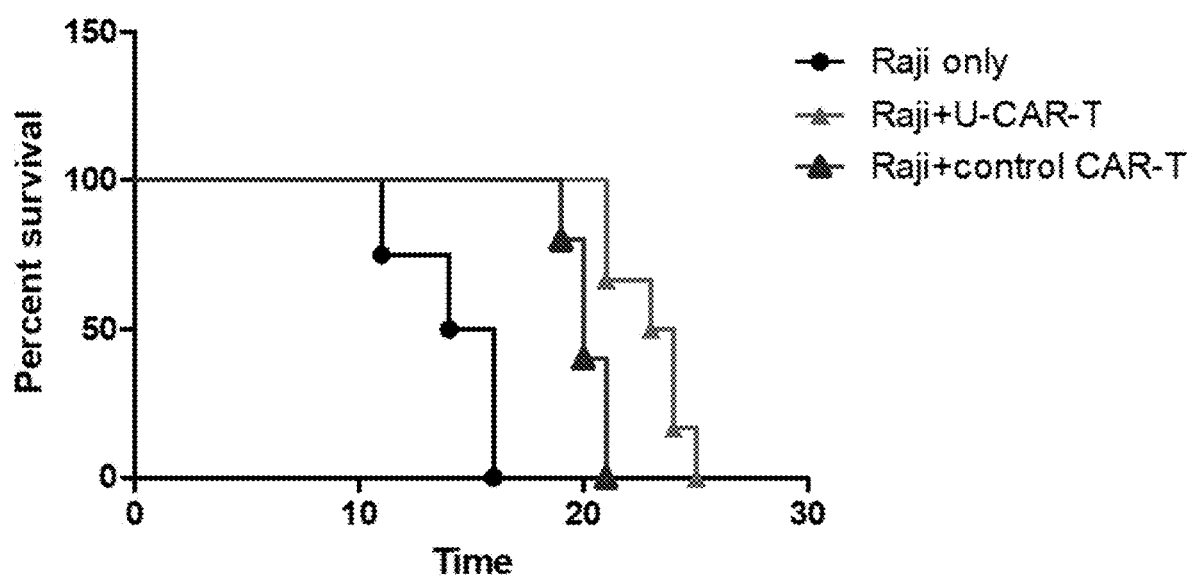
FIG. 6 illustrates schematic view of the in vivo survival ability of the CD3-negative 20BBZ CAR-T cells and the control CAR-T cell in an embodiment of the present invention.

10$^6$ Raji tumor cells were intravenously inoculated into B-NDG mice. After 6 days, the mice were treated with 10$^7$ U-CAR-T or the control CAR-T, and observed for their survival rate. The results are shown in FIG. 6. It can be seen from the figure that both the U-CAR-T and the control CAR-T result in the prolonged survival time of the mice.

It can be seen from the aforesaid examples that, the universal CAR-T constructed by knockout of CD3 in the present invention exhibits a low graft-versus-host response (GVHD), and greatly enhances and expands the convenience of CAR-T cell therapy. Meanwhile, an HSV-TK is introduced, so that the U-CAR-T can be rapidly cleared from the body by the regulation of ganciclovir, thereby further improving the safety of the universal CAR-T.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A universal CAR-T cell in which one or more of CD3Delta, CD3Gamma, CD3 Epsilon and CD3 zeta is knocked out, wherein said CAR-T cell comprises a nucleic acid encoding a chimeric antigen receptor (CAR), and said CAR includes an extracellular antigen recognition domain, a hinge region, a transmembrane domain, and an intracellular signal transduction domain, wherein said CAR includes an anti-CD19 CAR, and said anti-CD19 CAR comprises the amino acid sequence set forth in SEQ ID NO: 25.

2. A universal CAR-T cell in which one or more of CD3Delta, CD3Gamma, CD3 Epsilon and CD3 zeta is knocked out, wherein said CAR-T cell comprises a nucleic acid comprising the nucleotide sequence set forth in SEQ ID NO: 23 or SEQ ID NO: 29.

3. The universal CAR-T cell according to claim 1, wherein said CAR-T cell is derived from cord blood or peripheral blood.

4. A formulation comprising said universal CAR-T cell according to claim 1.

5. A method of treating a CD19 positive tumor in a subject in need thereof, comprising administering said universal CAR-T cell according to claim 1 to the subject.

* * * * *

SEQUENCE LISTING

```
<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: KO CD3Delta sgRNA1

<400> SEQUENCE: 1
gaacatagca cgtttctctc                                                    20

<210> SEQ ID NO 2
<211> LENGTH: 20
<212> TYPE: DNA
<213> ORGANISM: Artificial Sequence
<220> FEATURE:
<223> OTHER INFORMATION: KO CD3Delta sgRNA2

<400> SEQUENCE: 2
ccccttcaag atacctatag                                                    20

<210> SEQ ID NO 3
<211> LENGTH: 20
<212> TYPE: DNA
<213> ORGANISM: Artificial Sequence
<220> FEATURE:
<223> OTHER INFORMATION: KO CD3Gamma sgRNA1

<400> SEQUENCE: 3
ggctatcatt cttcttcaag                                                    20

<210> SEQ ID NO 4
<211> LENGTH: 20
<212> TYPE: DNA
<213> ORGANISM: Artificial Sequence
<220> FEATURE:
<223> OTHER INFORMATION: KO CD3Gamma sgRNA2

<400> SEQUENCE: 4
cttggttaag gtgtatgact                                                    20

<210> SEQ ID NO 5
<211> LENGTH: 20
<212> TYPE: DNA
<213> ORGANISM: Artificial Sequence
<220> FEATURE:
<223> OTHER INFORMATION: KO CD3Gamma sgRNA3

<400> SEQUENCE: 5
gtaatgccaa ggaccctcga                                                    20
```

<210> SEQ ID NO 6
<211> LENGTH: 20
<212> TYPE: DNA
<213> ORGANISM: Artificial Sequence
<220> FEATURE:
<223> OTHER INFORMATION: KO CD3 Epsilon sgRNA1

<400> SEQUENCE: 6
gggcactcac tggagagttc                                          20

<210> SEQ ID NO 7
<211> LENGTH: 20
<212> TYPE: DNA
<213> ORGANISM: Artificial Sequence
<220> FEATURE:
<223> OTHER INFORMATION: KO CD3 Epsilon sgRNA2

<400> SEQUENCE: 7
ttgacatgcc ctcagtatcc                                          20

<210> SEQ ID NO 8
<211> LENGTH: 20
<212> TYPE: DNA
<213> ORGANISM: Artificial Sequence
<220> FEATURE:
<223> OTHER INFORMATION: KO CD3 zeta sgRNA1

<400> SEQUENCE: 8
gtggaaggcg cttttcaccg                                          20

<210> SEQ ID NO 9
<211> LENGTH: 20
<212> TYPE: DNA
<213> ORGANISM: Artificial Sequence
<220> FEATURE:
<223> OTHER INFORMATION: KO CD3 zeta sgRNA2

<400> SEQUENCE: 9
tttcaccgcg gccatcctgc                                          20

<210> SEQ ID NO 10
<211> LENGTH: 20
<212> TYPE: DNA
<213> ORGANISM: Artificial Sequence
<220> FEATURE:
<223> OTHER INFORMATION: KO CD3 zeta sgRNA3

<400> SEQUENCE: 10
gatggaatcc tcttcatcta                                          20

<210> SEQ ID NO 11
<211> LENGTH: 241
<212> TYPE: PRT
<213> ORGANISM: Artificial Sequence
<220> FEATURE:
<223> OTHER INFORMATION: anti-CD20 scFv

<400> SEQUENCE: 11

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
         50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Gly Gly Gly Ser Gly
             100                 105                 110

Gly Gly Gly Ser Gly Gly Gly Ser Gln Val Gln Leu Gln Gln Pro
         115                 120                 125

Gly Ala Glu Leu Val Lys Pro Gly Ala Ser Val Lys Met Ser Cys Lys
        130                 135                 140

Ala Ser Gly Tyr Thr Phe Thr Ser Tyr Asn Met His Trp Val Lys Gln
145                 150                 155                 160

Thr Pro Gly Arg Gly Leu Glu Trp Ile Gly Ala Ile Tyr Pro Gly Asn
                165                 170                 175

Gly Asp Thr Ser Tyr Asn Gln Lys Phe Lys Gly Lys Ala Thr Leu Thr
            180                 185                 190

Ala Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Ser Thr Tyr Tyr Gly
210                 215                 220

Gly Asp Trp Tyr Phe Asn Val Trp Gly Ala Gly Thr Thr Val Thr Val
225                 230                 235                 240

Ser

<210> SEQ ID NO 12
<211> LENGTH: 45
<212> TYPE: PRT
<213> ORGANISM: Artificial Sequence
<220> FEATURE:
<223> OTHER INFORMATION: CD8a Hinge

<400> SEQUENCE: 12

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 13
<211> LENGTH: 24
<212> TYPE: PRT
<213> ORGANISM: Artificial Sequence
<220> FEATURE:
<223> OTHER INFORMATION: CD8a transmembrane domain

<400> SEQUENCE: 13

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 14
<211> LENGTH: 42
<212> TYPE: PRT
<213> ORGANISM: Artificial Sequence

```
<220> FEATURE:
<223> OTHER INFORMATION: 4-1BB

<400> SEQUENCE: 14

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 15
<211> LENGTH: 112
<212> TYPE: PRT
<213> ORGANISM: Artificial Sequence
<220> FEATURE:
<223> OTHER INFORMATION: CD3zeta

<400> SEQUENCE: 15

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 16
<211> LENGTH: 22
<212> TYPE: PRT
<213> ORGANISM: Artificial Sequence
<220> FEATURE:
<223> OTHER INFORMATION: the kappa leader sequence

<400> SEQUENCE: 16

Met Glu Thr Asp Thr Leu Leu Leu Trp Val Leu Leu Leu Trp Val Pro
1               5                   10                  15

Gly Ser Thr Gly Thr Gly
            20

<210> SEQ ID NO 17
<211> LENGTH: 21
<212> TYPE: PRT
<213> ORGANISM: Artificial Sequence
<220> FEATURE:
<223> OTHER INFORMATION: CD8 signal peptide

<400> SEQUENCE: 17

Met Ala Leu Pro Val Thr Ala Leu Leu Leu Pro Leu Ala Leu Leu Leu
1               5                   10                  15

His Ala Ala Arg Pro
            20

<210> SEQ ID NO 18
```

<211> LENGTH: 490
<212> TYPE: PRT
<213> ORGANISM: Artificial Sequence
<220> FEATURE:
<223> OTHER INFORMATION: anti-CD20 CAR

<400> SEQUENCE: 18

```
Met Glu Thr Asp Thr Leu Leu Leu Trp Val Leu Leu Leu Trp Val Pro
1               5                   10                  15

Gly Ser Thr Gly Thr Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125

Gly Gly Gly Gly Ser Gly Gly Gly Gly Gly Gly Gly Ser Gln
    130                 135                 140

Val Gln Leu Gln Gln Pro Gly Ala Glu Leu Val Lys Pro Gly Ala Ser
145                 150                 155                 160

Val Lys Met Ser Cys Lys Ala Ser Gly Tyr Thr Phe Thr Ser Tyr Asn
                165                 170                 175

Met His Trp Val Lys Gln Thr Pro Gly Arg Gly Leu Glu Trp Ile Gly
            180                 185                 190

Ala Ile Tyr Pro Gly Asn Gly Asp Thr Ser Tyr Asn Gln Lys Phe Lys
        195                 200                 205

Gly Lys Ala Thr Leu Thr Ala Asp Lys Ser Ser Ser Thr Ala Tyr Met
    210                 215                 220

Gln Leu Ser Ser Leu Thr Ser Glu Asp Ser Ala Val Tyr Tyr Cys Ala
225                 230                 235                 240

Arg Ser Thr Tyr Tyr Gly Gly Asp Trp Tyr Phe Asn Val Trp Gly Ala
                245                 250                 255

Gly Thr Thr Val Thr Val Ser Ala Ala Ala Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380
```

```
Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 19
<211> LENGTH: 22
<212> TYPE: PRT
<213> ORGANISM: Artificial Sequence
<220> FEATURE:
<223> OTHER INFORMATION: 2A

<400> SEQUENCE: 19

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 20
<211> LENGTH: 376
<212> TYPE: PRT
<213> ORGANISM: Artificial Sequence
<220> FEATURE:
<223> OTHER INFORMATION: TK

<400> SEQUENCE: 20

Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
                20                  25                  30

Arg Gln Gln Glu Ala Thr Glu Val Arg Leu Glu Gln Lys Met Pro Thr
            35                  40                  45

Leu Leu Arg Val Tyr Ile Asp Gly Pro His Gly Met Gly Lys Thr Thr
50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
                100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Val Gly
            130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
```

```
                          165                 170                 175
Tyr Leu Met Gly Ser Met Thr Pro Gln Ala Val Leu Ala Phe Val Ala
                180                 185                 190

Leu Ile Pro Pro Thr Leu Pro Gly Thr Asn Ile Val Leu Gly Ala Leu
            195                 200                 205

Pro Glu Asp Arg His Ile Asp Arg Leu Ala Lys Arg Gln Arg Pro Gly
        210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Trp
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 21
<211> LENGTH: 890
<212> TYPE: PRT
<213> ORGANISM: Artificial Sequence
<220> FEATURE:
<223> OTHER INFORMATION: 20BBZ-2A-TK

<400> SEQUENCE: 21

Met Glu Thr Asp Thr Leu Leu Leu Trp Val Leu Leu Leu Trp Val Pro
1               5                   10                  15

Gly Ser Thr Gly Thr Gly Gln Ile Val Leu Ser Gln Ser Pro Ala Ile
                20                  25                  30

Leu Ser Ala Ser Pro Gly Glu Lys Val Thr Met Thr Cys Arg Ala Ser
            35                  40                  45

Ser Ser Val Ser Tyr Ile His Trp Phe Gln Gln Lys Pro Gly Ser Ser
        50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
                100                 105                 110

Thr Ser Asn Pro Pro Thr Phe Gly Gly Gly Thr Lys Leu Glu Ile Lys
            115                 120                 125

Gly Gly Gly Gly Ser Gly Gly Gly Ser Gly Gly Gly Gly Ser Gln
        130                 135                 140

Val Gln Leu Gln Gln Pro Gly Ala Glu Leu Val Lys Pro Gly Ala Ser
```

-continued

```
            145                 150                 155                 160
        Val Lys Met Ser Cys Lys Ala Ser Gly Tyr Thr Phe Thr Ser Tyr Asn
                        165                 170                 175
        Met His Trp Val Lys Gln Thr Pro Gly Arg Gly Leu Glu Trp Ile Gly
                        180                 185                 190
        Ala Ile Tyr Pro Gly Asn Gly Asp Thr Ser Tyr Asn Gln Lys Phe Lys
                        195                 200                 205
        Gly Lys Ala Thr Leu Thr Ala Asp Lys Ser Ser Thr Ala Tyr Met
                        210                 215                 220
        Gln Leu Ser Ser Leu Thr Ser Glu Asp Ser Ala Val Tyr Tyr Cys Ala
        225                 230                 235                 240
        Arg Ser Thr Tyr Tyr Gly Gly Asp Trp Tyr Phe Asn Val Trp Gly Ala
                        245                 250                 255
        Gly Thr Thr Val Thr Val Ser Ala Ala Ala Thr Thr Thr Pro Ala
                        260                 265                 270
        Pro Arg Pro Pro Thr Pro Ala Pro Thr Ile Ala Ser Gln Pro Leu Ser
                        275                 280                 285
        Leu Arg Pro Glu Ala Cys Arg Pro Ala Ala Gly Gly Ala Val His Thr
        290                 295                 300
        Arg Gly Leu Asp Phe Ala Cys Asp Ile Tyr Ile Trp Ala Pro Leu Ala
        305                 310                 315                 320
        Gly Thr Cys Gly Val Leu Leu Leu Ser Leu Val Ile Thr Leu Tyr Cys
                        325                 330                 335
        Lys Arg Gly Arg Lys Lys Leu Leu Tyr Ile Phe Lys Gln Pro Phe Met
                        340                 345                 350
        Arg Pro Val Gln Thr Thr Gln Glu Glu Asp Gly Cys Ser Cys Arg Phe
                        355                 360                 365
        Pro Glu Glu Glu Glu Gly Gly Cys Glu Leu Arg Val Lys Phe Ser Arg
                        370                 375                 380
        Ser Ala Asp Ala Pro Ala Tyr Gln Gln Gly Gln Asn Gln Leu Tyr Asn
        385                 390                 395                 400
        Glu Leu Asn Leu Gly Arg Arg Glu Glu Tyr Asp Val Leu Asp Lys Arg
                        405                 410                 415
        Arg Gly Arg Asp Pro Glu Met Gly Gly Lys Pro Arg Arg Lys Asn Pro
                        420                 425                 430
        Gln Glu Gly Leu Tyr Asn Glu Leu Gln Lys Asp Lys Met Ala Glu Ala
                        435                 440                 445
        Tyr Ser Glu Ile Gly Met Lys Gly Glu Arg Arg Arg Gly Lys Gly His
                        450                 455                 460
        Asp Gly Leu Tyr Gln Gly Leu Ser Thr Ala Thr Lys Asp Thr Tyr Asp
        465                 470                 475                 480
        Ala Leu His Met Gln Ala Leu Pro Pro Arg Gly Ser Gly Ala Thr Asn
                        485                 490                 495
        Phe Ser Leu Leu Lys Gln Ala Gly Asp Val Glu Glu Asn Pro Gly Pro
                        500                 505                 510
        Arg Thr Met Ala Ser Tyr Pro Cys His Gln His Ala Ser Ala Phe Asp
                        515                 520                 525
        Gln Ala Ala Arg Ser Arg Gly His Ser Asn Arg Arg Thr Ala Leu Arg
        530                 535                 540
        Pro Arg Arg Gln Gln Glu Ala Thr Glu Val Arg Leu Glu Gln Lys Met
        545                 550                 555                 560
        Pro Thr Leu Leu Arg Val Tyr Ile Asp Gly Pro His Gly Met Gly Lys
                        565                 570                 575
```

```
Thr Thr Thr Thr Gln Leu Leu Val Ala Leu Gly Ser Arg Asp Asp Ile
            580                 585                 590

Val Tyr Val Pro Glu Pro Met Thr Tyr Trp Gln Val Leu Gly Ala Ser
        595                 600                 605

Glu Thr Ile Ala Asn Ile Tyr Thr Thr Gln His Arg Leu Asp Gln Gly
    610                 615                 620

Glu Ile Ser Ala Gly Asp Ala Ala Val Val Met Thr Ser Ala Gln Ile
625                 630                 635                 640

Thr Met Gly Met Pro Tyr Ala Val Thr Asp Ala Val Leu Ala Pro His
                645                 650                 655

Val Gly Gly Glu Ala Gly Ser Ser His Ala Pro Pro Ala Leu Thr
            660                 665                 670

Leu Ile Phe Asp Arg His Pro Ile Ala Ala Leu Leu Cys Tyr Pro Ala
        675                 680                 685

Ala Arg Tyr Leu Met Gly Ser Met Thr Pro Gln Ala Val Leu Ala Phe
    690                 695                 700

Val Ala Leu Ile Pro Pro Thr Leu Pro Gly Thr Asn Ile Val Leu Gly
705                 710                 715                 720

Ala Leu Pro Glu Asp Arg His Ile Asp Arg Leu Ala Lys Arg Gln Arg
                725                 730                 735

Pro Gly Glu Arg Leu Asp Leu Ala Met Leu Ala Ala Ile Arg Arg Val
            740                 745                 750

Tyr Gly Leu Leu Ala Asn Thr Val Arg Tyr Leu Gln Gly Gly Gly Ser
        755                 760                 765

Trp Trp Glu Asp Trp Gly Gln Leu Ser Gly Thr Ala Val Pro Pro Gln
    770                 775                 780

Gly Ala Glu Pro Gln Ser Asn Ala Gly Pro Arg Pro His Ile Gly Asp
785                 790                 795                 800

Thr Leu Phe Thr Leu Phe Arg Ala Pro Glu Leu Leu Ala Pro Asn Gly
                805                 810                 815

Asp Leu Tyr Asn Val Phe Ala Trp Ala Leu Asp Val Leu Ala Lys Arg
            820                 825                 830

Leu Arg Pro Met His Val Phe Ile Leu Asp Tyr Asp Gln Ser Pro Ala
        835                 840                 845

Gly Cys Arg Asp Ala Leu Leu Gln Leu Thr Ser Gly Met Val Gln Thr
    850                 855                 860

His Val Thr Thr Pro Gly Ser Ile Pro Thr Ile Cys Asp Leu Ala Arg
865                 870                 875                 880

Thr Phe Ala Arg Glu Met Gly Glu Ala Asn
                885                 890

<210> SEQ ID NO 22
<211> LENGTH: 1470
<212> TYPE: DNA
<213> ORGANISM: Artificial Sequence
<220> FEATURE:
<223> OTHER INFORMATION: Gene encoding anti-CD20 CAR

<400> SEQUENCE: 22
atggagaccg acaccctctt attatgggtg ctgttattat gggtccccgg aagcaccgga      60
accggtcaga tcgtgctgag ccagagcccc gccattctgt ccgccagccc cggcgagaag     120
gtgaccatga catgcagagc ctcctcctcc gtgagctaca tccactggtt ccagcagaag     180
cccggctcct cccctaagcc ttggatctac gccaccagca tctggctag cggagtgccc     240
```

```
gtgagattca gcggcagcgg aagcggaacc agctactctc tgaccatcag cagagtggag        300
gccgaggacg ccgctaccta ctactgtcag cagtggacca gcaaccctcc taccttcggc        360
ggcggcacca agctggagat caagggcgga ggaggctccg gaggtggagg ttctggcggt        420
ggaggttccc aagtgcagct gcagcagccc ggcgctgagc tggtgaaacc cggcgcttcc        480
gtgaagatga gctgcaaggc cagcggctac accttcacca gctacaacat gcactgggtg        540
aagcagaccc ccggcagagg actggaatgg atcggcgcca tttacccegg caacggcgat        600 acctcctaca accagaagtt caagggcaag gctacactga ccgccgacaa gagcagcagc        660
accgcctaca tgcagctgag ctctctgacc agcgaggaca cgccgtgta ctactgcgct        720 agaagcacct actacggcgg cgactggtac ttcaacgtgt ggggagccgg cacaaccgtg        780
acagtgtccg ccgcggccgc tacaaccacc cccgctccca gacctcctac acccgctccc        840
accattgcca gccagcctct ctctttaaga cccgaggctt gtaggccgc tgctggagga        900 gccgtgcaca aaggggact ggactttgct tgtgatatct atatctgggc ccctctggct        960
ggaacttgtg gagtcctctt attatcttta gtgatcactt tatactgtaa gaggggtcgt       1020
aagaagttat tatacatctt caagcagccc ttcatgaggc ccgtccaaac cacccaagaa       1080
gaggacggat gtagctgtag gtttcccgag gaggaggagg aggctgcga attacgtgtc       1140 aagttctcca gaagcgccga tgccccgct taccaacaag gtcagaacca gctgtacaat       1200
gagctgaatc tgggcagaag agaagagtac gacgtgctgg ataagaggag gggtcgtgac       1260
cccgaaatgg gaggcaagcc cagaagaaaa accccccaag aaggactcta caacgagctg       1320
caaaaggata gatggctga ggcctattcc gagattggca tgaagggcga gagaaggaga       1380
ggcaagggcc acgacggttt atatcaaggt ctctccaccg ccaccaagga cacatacgat       1440
gctctgcaca tgcaagctct gccccccaga                                        1470

<210> SEQ ID NO 23
<211> LENGTH: 2673
<212> TYPE: DNA
<213> ORGANISM: Artificial Sequence
<220> FEATURE:
<223> OTHER INFORMATION: Gene encoding anti-CD20 CAR and HSV-TK

<400> SEQUENCE: 23
atggagaccg acaccctctt attatgggtg ctgttattat ggtcccccgg aagcaccgga         60
accggtcaga tcgtgctgag ccagagcccc gccattctgt ccgccagccc cggcgagaag        120
gtgaccatga catgcagagc ctcctcctcc gtgagctaca tccactggtt ccagcagaag        180
cccggctcct cccctaagcc ttggatctac gccaccagca atctggctag cggagtgccc        240
gtgagattca gcggcagcgg aagcggaacc agctactctc tgaccatcag cagagtggag        300
gccgaggacg ccgctaccta ctactgtcag cagtggacca gcaaccctcc taccttcggc        360
ggcggcacca agctggagat caagggcgga ggaggctccg gaggtggagg ttctggcggt        420
ggaggttccc aagtgcagct gcagcagccc ggcgctgagc tggtgaaacc cggcgcttcc        480
gtgaagatga gctgcaaggc cagcggctac accttcacca gctacaacat gcactgggtg        540
aagcagaccc ccggcagagg actggaatgg atcggcgcca tttacccegg caacggcgat        600 acctcctaca accagaagtt caagggcaag gctacactga ccgccgacaa gagcagcagc        660
accgcctaca tgcagctgag ctctctgacc agcgaggaca cgccgtgta ctactgcgct        720 agaagcacct actacggcgg cgactggtac ttcaacgtgt ggggagccgg cacaaccgtg        780
acagtgtccg ccgcggccgc tacaaccacc cccgctccca gacctcctac acccgctccc        840
```

```
accattgcca gccagcctct ctctttaaga cccgaggctt gtaggcccgc tgctggagga    900
gccgtgcaca aagggact  ggactttgct tgtgatatct atatctgggc cctctggct     960
```

| | |
|---|---|
| accattgcca gccagcctct ctctttaaga cccgaggctt gtaggcccgc tgctggagga | 900 |
| gccgtgcaca aaggggact ggactttgct tgtgatatct atatctgggc cctctggct | 960 |
| ggaacttgtg gagtcctctt attatcttta gtgatcactt tatactgtaa gagggggtcgt | 1020 |
| aagaagttat tatacatctt caagcagccc ttcatgaggc ccgtccaaac cacccaagaa | 1080 |
| gaggacggat gtagctgtag gtttcccgag gaggaggagg gaggctgcga attacgtgtc | 1140 |
| aagttctcca gaagcgccga tgccccgct taccaacaag gtcagaacca gctgtacaat | 1200 |
| gagctgaatc tgggcagaag agaagagtac gacgtgctgg ataagaggag ggtcgtgac | 1260 |
| cccgaaatgg gaggcaagcc cagaagaaaa accccccaag aaggactcta acgagctg | 1320 |
| caaaaggata gatggctga ggcctattcc gagattggca tgaagggcga gagaaggaga | 1380 |
| ggcaagggcc acgacggttt atatcaaggt ctctccaccg ccaccaagga cacatacgat | 1440 |
| gctctgcaca tgcaagctct gccccccaga ggctccggcg ccacaaactt ctctttactg | 1500 |
| aagcaagctg gagacgtgga ggagaacccc ggtcctcgta cgatggccag ctacccttgc | 1560 |
| catcagcacg ccagcgcttt cgaccaagct gccagatcca gaggccacag caacagaagg | 1620 |
| accgctttaa gacctagaag gcaacaagaa gctacagagg tgagattaga acaaaagatg | 1680 |
| cccaccttat taagggtgta catcgacgga cctcacggca tgggaaaaac cacaactacc | 1740 |
| caactgctgg tggctctggg cagcagagac gatatcgtct atgtgcccga acccatgacc | 1800 |
| tactggcaag tgctcggcgc ctctgagacc atcgccaaca tctacacaac ccagcatagg | 1860 |
| ctcgaccaag tgaaatctc cgccggcgat gctgccgtgg tgatgaccag cgcccagatc | 1920 |
| acaatgggca tgccctacgc cgtgacagat gctgttttag ccccccatgt cggaggagag | 1980 |
| gctggaagct cccatgcccc tcctcccgct ctcacactga ttttcgatcg tcatcccatt | 2040 |
| gccgctctgc tgtgttatcc cgccgccaga tatttaatgg gcagcatgac accccaagcc | 2100 |
| gtgctggcct ttgtggccct catccccccc actttacccg gtaccaatat cgtgctggga | 2160 |
| gctctccccg aggataggca tattgataga ctggccaaga ggcagaggcc cggcgaaaga | 2220 |
| ctcgatctgg ccatgctggc cgccattaga agggtgtacg gattattagc caacacagtt | 2280 |
| cgttatttac aaggtggcgg cagctggtgg gaagattggg gacagctgtc cggcacagct | 2340 |
| gtgcctcctc aaggtgccga accccaatcc aacgccggac ctagacccca tcggcgac | 2400 |
| actttattca ccctctttcg tgcccccgaa ttattagccc ccaatggaga tttatacaac | 2460 |
| gtgtttgctt gggctttaga tgtgctggcc aaaagactga gacctatgca tgtcttcatc | 2520 |
| ctcgattatg atcagtcccc cgccggatgt cgtgacgctt tactgcagct cacatccgga | 2580 |
| atggtgcaga cccacgtcac aacacccggc agcatcccca ccatctgcga tttagctaga | 2640 |
| accttcgctc gtgagatggg cgaggccaac taa | 2673 |

<210> SEQ ID NO 24
<211> LENGTH: 242
<212> TYPE: PRT
<213> ORGANISM: Artificial Sequence
<220> FEATURE:
<223> OTHER INFORMATION: anti-CD19 scFv

<400> SEQUENCE: 24

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

```
Leu Asn Trp Tyr Gln Gln Lys Pro Asp Gly Thr Val Lys Leu Leu Ile
             35                  40                  45

Tyr His Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Gly Gly Gly Gly Ser
                100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
                180                 185                 190

Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Tyr Gly
        210                 215                 220

Gly Ser Tyr Ala Met Asp Tyr Trp Gly Gln Gly Thr Ser Val Thr Val
225                 230                 235                 240

Ser Ser

<210> SEQ ID NO 25
<211> LENGTH: 491
<212> TYPE: PRT
<213> ORGANISM: Artificial Sequence
<220> FEATURE:
<223> OTHER INFORMATION: anti-CD19 CAR

<400> SEQUENCE: 25

Met Glu Thr Asp Thr Leu Leu Leu Trp Val Leu Leu Leu Trp Val Pro
 1               5                  10                  15

Gly Ser Thr Gly Thr Gly Asp Ile Gln Met Thr Gln Thr Thr Ser Ser
                20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
 50                  55                  60

Thr Val Lys Leu Leu Ile Tyr His Thr Ser Arg Leu His Ser Gly Val
 65                  70                  75                  80

Pro Ser Arg Phe Ser Gly Ser Gly Ser Gly Thr Asp Tyr Ser Leu Thr
                 85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
130                 135                 140

Glu Val Lys Leu Gln Glu Ser Gly Pro Gly Leu Val Ala Pro Ser Gln
```

```
                145                 150                 155                 160
        Ser Leu Ser Val Thr Cys Thr Val Ser Gly Val Ser Leu Pro Asp Tyr
                        165                 170                 175

Gly Val Ser Trp Ile Arg Gln Pro Pro Arg Lys Gly Leu Glu Trp Leu
                        180                 185                 190

Gly Val Ile Trp Gly Ser Glu Thr Thr Tyr Tyr Asn Ser Ala Leu Lys
                        195                 200                 205

Ser Arg Leu Thr Ile Ile Lys Asp Asn Ser Lys Ser Gln Val Phe Leu
                210                 215                 220

Lys Met Asn Ser Leu Gln Thr Asp Asp Thr Ala Ile Tyr Tyr Cys Ala
        225                 230                 235                 240

Lys His Tyr Tyr Tyr Gly Gly Ser Tyr Ala Met Asp Tyr Trp Gly Gln
                        245                 250                 255

Gly Thr Ser Val Thr Val Ser Ser Ala Ala Ala Thr Thr Thr Pro
                        260                 265                 270

Ala Pro Arg Pro Pro Thr Pro Ala Pro Thr Ile Ala Ser Gln Pro Leu
                        275                 280                 285

Ser Leu Arg Pro Glu Ala Cys Arg Pro Ala Ala Gly Gly Ala Val His
                290                 295                 300

Thr Arg Gly Leu Asp Phe Ala Cys Asp Ile Tyr Ile Trp Ala Pro Leu
        305                 310                 315                 320

Ala Gly Thr Cys Gly Val Leu Leu Leu Ser Leu Val Ile Thr Leu Tyr
                        325                 330                 335

Cys Lys Arg Gly Arg Lys Lys Leu Leu Tyr Ile Phe Lys Gln Pro Phe
                        340                 345                 350

Met Arg Pro Val Gln Thr Thr Gln Glu Glu Asp Gly Cys Ser Cys Arg
                        355                 360                 365

Phe Pro Glu Glu Glu Glu Gly Gly Cys Glu Leu Arg Val Lys Phe Ser
                        370                 375                 380

Arg Ser Ala Asp Ala Pro Ala Tyr Gln Gln Gly Gln Asn Gln Leu Tyr
        385                 390                 395                 400

Asn Glu Leu Asn Leu Gly Arg Arg Glu Glu Tyr Asp Val Leu Asp Lys
                        405                 410                 415

Arg Arg Gly Arg Asp Pro Glu Met Gly Gly Lys Pro Arg Arg Lys Asn
                        420                 425                 430

Pro Gln Glu Gly Leu Tyr Asn Glu Leu Gln Lys Asp Lys Met Ala Glu
                        435                 440                 445

Ala Tyr Ser Glu Ile Gly Met Lys Gly Glu Arg Arg Arg Gly Lys Gly
                        450                 455                 460

His Asp Gly Leu Tyr Gln Gly Leu Ser Thr Ala Thr Lys Asp Thr Tyr
        465                 470                 475                 480

Asp Ala Leu His Met Gln Ala Leu Pro Pro Arg
                        485                 490

<210> SEQ ID NO 26
<211> LENGTH: 891
<212> TYPE: PRT
<213> ORGANISM: Artificial Sequence
<220> FEATURE:
<223> OTHER INFORMATION: 19BBZ-2A-TK

<400> SEQUENCE: 26

Met Glu Thr Asp Thr Leu Leu Leu Trp Val Leu Leu Leu Trp Val Pro
1               5                   10                  15

Gly Ser Thr Gly Thr Gly Asp Ile Gln Met Thr Gln Thr Thr Ser Ser
```

```
                    20                  25                  30
Leu Ser Ala Ser Leu Gly Asp Arg Val Thr Ile Ser Cys Arg Ala Ser
            35                  40                  45
Gln Asp Ile Ser Lys Tyr Leu Asn Trp Tyr Gln Gln Lys Pro Asp Gly
        50                  55                  60
Thr Val Lys Leu Leu Ile Tyr His Thr Ser Arg Leu His Ser Gly Val
65                  70                  75                  80
Pro Ser Arg Phe Ser Gly Ser Gly Ser Gly Thr Asp Tyr Ser Leu Thr
                85                  90                  95
Ile Ser Asn Leu Glu Gln Glu Asp Ile Ala Thr Tyr Phe Cys Gln Gln
            100                 105                 110
Gly Asn Thr Leu Pro Tyr Thr Phe Gly Gly Gly Thr Lys Leu Glu Ile
        115                 120                 125
Thr Gly Gly Gly Gly Ser Gly Gly Gly Ser Gly Gly Gly Gly Ser
        130                 135                 140
Glu Val Lys Leu Gln Glu Ser Gly Pro Gly Leu Val Ala Pro Ser Gln
145                 150                 155                 160
Ser Leu Ser Val Thr Cys Thr Val Ser Gly Val Ser Leu Pro Asp Tyr
                165                 170                 175
Gly Val Ser Trp Ile Arg Gln Pro Pro Arg Lys Gly Leu Glu Trp Leu
            180                 185                 190
Gly Val Ile Trp Gly Ser Glu Thr Thr Tyr Tyr Asn Ser Ala Leu Lys
        195                 200                 205
Ser Arg Leu Thr Ile Ile Lys Asp Asn Ser Lys Ser Gln Val Phe Leu
    210                 215                 220
Lys Met Asn Ser Leu Gln Thr Asp Asp Thr Ala Ile Tyr Tyr Cys Ala
225                 230                 235                 240
Lys His Tyr Tyr Tyr Gly Gly Ser Tyr Ala Met Asp Tyr Trp Gly Gln
                245                 250                 255
Gly Thr Ser Val Thr Val Ser Ser Ala Ala Ala Thr Thr Thr Pro
            260                 265                 270
Ala Pro Arg Pro Pro Thr Pro Ala Pro Thr Ile Ala Ser Gln Pro Leu
        275                 280                 285
Ser Leu Arg Pro Glu Ala Cys Arg Pro Ala Ala Gly Gly Ala Val His
    290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Leu Tyr
                325                 330                 335
Cys Lys Arg Gly Arg Lys Lys Leu Leu Tyr Ile Phe Lys Gln Pro Phe
            340                 345                 350
Met Arg Pro Val Gln Thr Thr Gln Glu Glu Asp Gly Cys Ser Cys Arg
        355                 360                 365
Phe Pro Glu Glu Glu Glu Gly Gly Cys Glu Leu Arg Val Lys Phe Ser
    370                 375                 380
Arg Ser Ala Asp Ala Pro Ala Tyr Gln Gln Gly Gln Asn Gln Leu Tyr
385                 390                 395                 400
Asn Glu Leu Asn Leu Gly Arg Arg Glu Glu Tyr Asp Val Leu Asp Lys
                405                 410                 415
Arg Arg Gly Arg Asp Pro Glu Met Gly Gly Lys Pro Arg Arg Lys Asn
            420                 425                 430
Pro Gln Glu Gly Leu Tyr Asn Glu Leu Gln Lys Asp Lys Met Ala Glu
        435                 440                 445
```

```
Ala Tyr Ser Glu Ile Gly Met Lys Gly Glu Arg Arg Gly Lys Gly
            450                 455                 460

His Asp Gly Leu Tyr Gln Gly Leu Ser Thr Thr Lys Asp Thr Tyr
465                 470                 475                 480

Asp Ala Leu His Met Gln Ala Leu Pro Pro Arg Gly Ser Gly Ala Thr
                    485                 490                 495

Asn Phe Ser Leu Leu Lys Gln Ala Gly Asp Val Glu Glu Asn Pro Gly
                500                 505                 510

Pro Arg Thr Met Ala Ser Tyr Pro Cys His Gln His Ala Ser Ala Phe
                515                 520                 525

Asp Gln Ala Ala Arg Ser Arg Gly His Ser Asn Arg Thr Ala Leu
530                 535                 540

Arg Pro Arg Arg Gln Gln Glu Ala Thr Glu Val Arg Leu Glu Gln Lys
545                 550                 555                 560

Met Pro Thr Leu Leu Arg Val Tyr Ile Asp Gly Pro His Gly Met Gly
                565                 570                 575

Lys Thr Thr Thr Thr Gln Leu Leu Val Ala Leu Gly Ser Arg Asp Asp
                580                 585                 590

Ile Val Tyr Val Pro Glu Pro Met Thr Tyr Trp Gln Val Leu Gly Ala
            595                 600                 605

Ser Glu Thr Ile Ala Asn Ile Tyr Thr Thr Gln His Arg Leu Asp Gln
            610                 615                 620

Gly Glu Ile Ser Ala Gly Asp Ala Ala Val Val Met Thr Ser Ala Gln
625                 630                 635                 640

Ile Thr Met Gly Met Pro Tyr Ala Val Thr Asp Ala Val Leu Ala Pro
                645                 650                 655

His Val Gly Gly Glu Ala Gly Ser Ser His Ala Pro Pro Ala Leu
            660                 665                 670

Thr Leu Ile Phe Asp Arg His Pro Ile Ala Ala Leu Leu Cys Tyr Pro
            675                 680                 685

Ala Ala Arg Tyr Leu Met Gly Ser Met Thr Pro Gln Ala Val Leu Ala
690                 695                 700

Phe Val Ala Leu Ile Pro Pro Thr Leu Pro Gly Thr Asn Ile Val Leu
705                 710                 715                 720

Gly Ala Leu Pro Glu Asp Arg His Ile Asp Arg Leu Ala Lys Arg Gln
                725                 730                 735

Arg Pro Gly Glu Arg Leu Asp Leu Ala Met Leu Ala Ala Ile Arg Arg
                740                 745                 750

Val Tyr Gly Leu Leu Ala Asn Thr Val Arg Tyr Leu Gln Gly Gly Gly
            755                 760                 765

Ser Trp Trp Glu Asp Trp Gly Gln Leu Ser Gly Thr Ala Val Pro Pro
770                 775                 780

Gln Gly Ala Glu Pro Gln Ser Asn Ala Gly Pro Arg Pro His Ile Gly
785                 790                 795                 800

Asp Thr Leu Phe Thr Leu Phe Arg Ala Pro Glu Leu Leu Ala Pro Asn
                805                 810                 815

Gly Asp Leu Tyr Asn Val Phe Ala Trp Ala Leu Asp Val Leu Ala Lys
                820                 825                 830

Arg Leu Arg Pro Met His Val Phe Ile Leu Asp Tyr Asp Gln Ser Pro
            835                 840                 845

Ala Gly Cys Arg Asp Ala Leu Leu Gln Leu Thr Ser Gly Met Val Gln
850                 855                 860
```

```
Thr His Val Thr Thr Pro Gly Ser Ile Pro Thr Ile Cys Asp Leu Ala
865                 870                 875                 880

Arg Thr Phe Ala Arg Glu Met Gly Glu Ala Asn
                885                 890
```

<210> SEQ ID NO 27
<211> LENGTH: 792
<212> TYPE: DNA
<213> ORGANISM: Artificial Sequence
<220> FEATURE:
<223> OTHER INFORMATION: Gene encoding anti-CD19 scFv

<400> SEQUENCE: 27

```
atggagaccg acaccctctt attatgggtg ctgttattat gggtcccgg aagcaccgga      60 accggtgata tccagatgac ccagaccacc tcctctttaa gcgcctcttt aggcgatagg    120
gtgaccatca gctgtagggc cagccaagat atctccaagt atttaaactg gtaccagcaa    180
aaacccgatg gcaccgtgaa gctgctcatc taccatacct ccagactgca ctccggagtg    240
ccctccagat tcagcggaag cggctccgga accgactata gcctcaccat ctccaattta    300
gagcaagaag atatcgccac ctacttctgt cagcaaggta acacactgcc ttacaccttc    360
ggcggaggca ccaagctgga aatcactggc ggaggaggct ccggaggtgg aggttctggc    420
ggtggaggtt ccgaagtgaa gctgcaagaa agcggccccg gtctcgtggc tccctcccag    480
tctttatccg tgacttgtac agtgagcggc gtctctttac ccgactatgg cgtctcttgg    540
attaggcagc ctcctcgtaa aggactggaa tggctgggag tcatctgggg cagcgagaca    600
acctactaca actccgcttt aaagtctcgt ctgaccatta ttaaggacaa cagcaaaagc    660
caagttttcc tcaagatgaa cagcctccag accgatgaca ccgctatcta ctactgcgct    720
aaacattact actacggcgg ctcctacgcc atggactact ggggacaagg tacctccgtg    780
acagtgtcca gc                                                        792
```

<210> SEQ ID NO 28
<211> LENGTH: 1473
<212> TYPE: DNA
<213> ORGANISM: Artificial Sequence
<220> FEATURE:
<223> OTHER INFORMATION: Gene encoding anti-CD19 CAR

<400> SEQUENCE: 28

```
atggagaccg acaccctctt attatgggtg ctgttattat gggtcccgg aagcaccgga      60 accggtgata tccagatgac ccagaccacc tcctctttaa gcgcctcttt aggcgatagg    120
gtgaccatca gctgtagggc cagccaagat atctccaagt atttaaactg gtaccagcaa    180
aaacccgatg gcaccgtgaa gctgctcatc taccatacct ccagactgca ctccggagtg    240
ccctccagat tcagcggaag cggctccgga accgactata gcctcaccat ctccaattta    300
gagcaagaag atatcgccac ctacttctgt cagcaaggta acacactgcc ttacaccttc    360
ggcggaggca ccaagctgga aatcactggc ggaggaggct ccggaggtgg aggttctggc    420
ggtggaggtt ccgaagtgaa gctgcaagaa agcggccccg gtctcgtggc tccctcccag    480
tctttatccg tgacttgtac agtgagcggc gtctctttac ccgactatgg cgtctcttgg    540
attaggcagc ctcctcgtaa aggactggaa tggctgggag tcatctgggg cagcgagaca    600
acctactaca actccgcttt aaagtctcgt ctgaccatta ttaaggacaa cagcaaaagc    660
caagttttcc tcaagatgaa cagcctccag accgatgaca ccgctatcta ctactgcgct    720
aaacattact actacggcgg ctcctacgcc atggactact ggggacaagg tacctccgtg    780
```

```
acagtgtcca gcgccgcggc cgctacaacc accccgctc ccagacctcc tacacccgct    840
cccaccattg ccagccagcc tctctcttta agacccgagg cttgtaggcc cgctgctgga    900
ggagccgtgc acacaagggg actggacttt gcttgtgata tctatatctg ggcccctctg    960
gctggaactt gtggagtcct cttattatct ttagtgatca ctttatactg taagaggggt   1020
cgtaagaagt tattatacat cttcaagcag cccttcatga ggcccgtcca aaccacccaa   1080
gaagaggacg gatgtagctg taggtttccc gaggaggagg agggaggctg cgaattacgt   1140
gtcaagttct ccagaagcgc cgatgccccc gcttaccaac aaggtcagaa ccagctgtac   1200
aatgagctga atctgggcag aagagaagag tacgacgtgc tggataagag gagggggtcgt   1260 gaccccgaaa tgggaggcaa gcccagaaga aaaaacccc aagaaggact ctacaacgag   1320
ctgcaaaagg ataagatggc tgaggcctat tccgagattg gcatgaaggg cgagagaagg   1380
agaggcaagg gccacgacgg tttatatcaa ggtctctcca ccgccaccaa ggacacatac   1440
gatgctctgc acatgcaagc tctgccccc aga                                1473

<210> SEQ ID NO 29
<211> LENGTH: 2676
<212> TYPE: DNA
<213> ORGANISM: Artificial Sequence
<220> FEATURE:
<223> OTHER INFORMATION: Gene encoding anti-CD19 CAR and HSV-TK

<400> SEQUENCE: 29
atggagaccg acaccctctt attatgggtg ctgttattat gggtccccgg aagcaccgga     60
accggtgata tccagatgac ccagaccacc tcctctttaa gcgcctcttt aggcgatagg    120
gtgaccatca gctgtagggc cagccaagat atctccaagt atttaaactg gtaccagcaa    180
aaacccgatg gcaccgtgaa gctgctcatc taccatacct ccagactgca ctccggagtg    240
ccctccagat tcagcggaag cggctccgga accgactata gcctcaccat ctccaattta    300
gagcaagaag atatcgccac ctacttctgt cagcaaggta acacactgcc ttacaccttc    360
ggcggaggca ccaagctgga aatcactggc ggaggaggct ccggaggtgg aggttctggc    420
ggtggaggtt ccgaagtgaa gctgcaagaa agcggccccg tctcgtggc tcctcccag    480 tctttatccg tgacttgtac agtgagcggc gtctctttac ccgactatgg cgtctcttgg    540
attaggcagc ctcctcgtaa aggactggaa tggctgggag tcatctgggg cagcgagaca   600
acctactaca actccgcttt aaagtctcgt ctgaccatta ttaaggacaa cagcaaaagc   660
caagttttcc tcaagatgaa cagcctccag accgatgaca ccgctatcta ctactgcgct   720
aaacattact actacggcgg ctcctacgcc atggactact ggggacaagg tacctccgtg   780
acagtgtcca gcgccgcggc cgctacaacc accccgctc ccagacctcc tacacccgct   840
cccaccattg ccagccagcc tctctcttta agacccgagg cttgtaggcc cgctgctgga   900
ggagccgtgc acacaagggg actggacttt gcttgtgata tctatatctg ggcccctctg   960
gctggaactt gtggagtcct cttattatct ttagtgatca ctttatactg taagaggggt  1020
cgtaagaagt tattatacat cttcaagcag cccttcatga ggcccgtcca aaccacccaa  1080
gaagaggacg gatgtagctg taggtttccc gaggaggagg agggaggctg cgaattacgt  1140
gtcaagttct ccagaagcgc cgatgccccc gcttaccaac aaggtcagaa ccagctgtac  1200
aatgagctga atctgggcag aagagaagag tacgacgtgc tggataagag gagggggtcgt  1260 gaccccgaaa tgggaggcaa gcccagaaga aaaaacccc aagaaggact ctacaacgag  1320
```

```
ctgcaaaagg ataagatggc tgaggcctat tccgagattg gcatgaaggg cgagagaagg    1380
agaggcaagg gccacgacgg tttatatcaa ggtctctcca ccgccaccaa ggacacatac    1440
gatgctctgc acatgcaagc tctgcccccc agaggctccg gcgccacaaa cttctcttta    1500
ctgaagcaag ctggagacgt ggaggagaac cccggtcctc gtacgatggc cagctaccct    1560
tgccatcagc acgccagcgc tttcgaccaa gctgccagat ccagaggcca cagcaacaga    1620
aggaccgctt taagacctag aaggcaacaa gaagctacag aggtgagatt agaacaaaag    1680
atgcccacct tattaagggt gtacatcgac ggaccctcac gcatgggaaa accacaact    1740 acccaactgc tggtggctct gggcagcaga cgcgatatcg tctatgtgcc cgaacccatg    1800
acctactggc aagtgctcgg cgcctctgag accatcgcca acatctacac aacccagcat    1860
aggctcgacc aaggtgaaat ctccgccggc gatgctgccg tggtgatgac cagcgcccag    1920
atcacaatgg gcatgcccta cgccgtgaca gatgctgttt tagccccca tgtcggagga    1980 gaggctggaa gctcccatgc ccctcctccc gctctcacac tgattttcga tcgtcatccc    2040
attgccgctc tgctgtgtta tccgccgcc agatatttaa tgggcagcat gacaccccaa    2100
gccgtgctgg cctttgtggc cctcatcccc ccactttac ccggtaccaa tatcgtgctg    2160
ggagctctcc ccgaggatag gcatattgat agactggcca agaggcagag gcccggcgaa    2220
agactcgatc tggccatgct ggccgccatt agaagggtgt acggattatt agccaacaca    2280
gttcgttatt tacaaggtgg cggcagctgg tgggaagatt ggggacagct gtccggcaca    2340
gctgtgcctc ctcaaggtgc cgaaccccaa tccaacgccg gacctagacc ccacatcggc    2400
gacactttat tcaccctctt tcgtgccccc gaattattag ccccaatgg agatttatac    2460 aacgtgtttg cttgggcttt agatgtgctg gccaaaagac tgagacctat gcatgtcttc    2520
atcctcgatt atgatcagtc ccccgccgga tgtcgtgacg ctttactgca gctcacatcc    2580
ggaatggtgc agacccacgt cacaacaccc ggcagcatcc ccaccatctg cgatttagct    2640
agaaccttcg ctcgtgagat gggcgaggcc aactaa                              2676

<210> SEQ ID NO 30
<211> LENGTH: 1137
<212> TYPE: DNA
<213> ORGANISM: Artificial Sequence
<220> FEATURE:
<223> OTHER INFORMATION: Gene encoding HSV-TK

<400> SEQUENCE: 30
cgtacgatgg ccagctaccc ttgccatcag cacgccagcg ctttcgacca agctgccaga      60
tccagaggcc acagcaacag aaggaccgct ttaagaccta gaaggcaaca agaagctaca     120
gaggtgagat tagaacaaaa gatgcccacc ttattaaggg tgtacatcga cggacctcac     180
ggcatgggaa aaccacaac tacccaactg ctggtggctc tgggcagcag agacgatatc     240
gtctatgtgc ccgaacccat gacctactgg caagtgctcg cgcctctga gaccatcgcc     300 aacatctaca acccagcta ggctcgac caaggtgaaa tctccgccgg cgatgctgcc      360
gtggtgatga ccagcgccca gatcacaatg gcatgccct acgccgtgac agatgctgtt     420
ttagcccccc atgtcggagg agaggctgga agctcccatg cccctcctcc cgctctcaca     480
ctgattttcg atcgtcatcc cattgccgct ctgctgtgtt atccgccgc cagatattta     540 atgggcagca tgacacccca agccgtgctg cctttgtgg ccctcatccc cccacttta     600 cccggtacca atatcgtgct gggagctctc ccgaggata ggcatattga tagactggcc     660
aagaggcaga ggcccggcga aagactcgat ctggccatgc tggccgccat tagaagggtg     720
```

-continued

```
tacggattat tagccaacac agttcgttat ttacaaggtg gcggcagctg gtgggaagat    780
tggggacagc tgtccggcac agctgtgcct cctcaaggtg ccgaacccca atccaacgcc    840
ggacctagac cccacatcgg cgacacttta ttcaccctct ttcgtgcccc cgaattatta    900
gcccccaatg gagatttata caacgtgttt gcttgggctt tagatgtgct ggccaaaaga    960
ctgagaccta tgcatgtctt catcctcgat tatgatcagt ccccgccgg atgtcgtgac   1020 gctttactgc agctcacatc cggaatggtg cagacccacg tcacaacacc cggcagcatc   1080
cccaccatct gcgatttagc tagaaccttc gctcgtgaga tgggcgaggc caactaa     1137
```